(12) United States Patent
Fukuyo et al.

(10) Patent No.: US 8,247,734 B2
(45) Date of Patent: Aug. 21, 2012

(54) LASER BEAM MACHINING METHOD

(75) Inventors: Fumitsugu Fukuyo, Hamamatsu (JP);
Kenshi Fukumitsu, Hamamatsu (JP);
Naoki Uchiyama, Hamamatsu (JP);
Toshimitsu Wakuda, Hamamatsu (JP);
Kazuhiro Atsumi, Hamamatsu (JP);
Kenichi Muramatsu, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 1276 days.

(21) Appl. No.: 10/547,976

(22) PCT Filed: Mar. 12, 2003

(86) PCT No.: PCT/JP03/02943
§ 371 (c)(1),
(2), (4) Date: Jul. 10, 2006

(87) PCT Pub. No.: WO2004/080642
PCT Pub. Date: Sep. 23, 2004

(65) Prior Publication Data
US 2006/0255024 A1    Nov. 16, 2006

(51) Int. Cl.
*H01L 21/301* (2006.01)
*H01L 21/322* (2006.01)
*H01L 21/78* (2006.01)

(52) U.S. Cl. .................. 219/121.66; 438/463

(58) Field of Classification Search ......... 219/121.67–121.71, 121.76, 121.85, 219/121.65, 121.66; 438/463
See application file for complete search history.

(56) References Cited

U.S. PATENT DOCUMENTS

| 3,448,510 | A | * | 6/1969 | Johnson, Jr et al. | 29/413 |
| 3,543,979 | A | | 12/1970 | Grove et al. | |
| 3,610,871 | A | | 10/1971 | Lumley | |
| 3,613,974 | A | | 10/1971 | Chatelain et al. | |
| 3,626,141 | A | * | 12/1971 | Daly | 219/121.68 |

(Continued)

FOREIGN PATENT DOCUMENTS

CN    1160228 A    9/1997

(Continued)

OTHER PUBLICATIONS

F. Fukuyo et al., "The Stealth Dicing Technologies and Their Applications," Journal of Japan Laser Processing Society, vol. 12, No. 1, Feb. 2005, pp. 17-23, with English translation.

(Continued)

*Primary Examiner* — Samuel M Heinrich
(74) *Attorney, Agent, or Firm* — Drinker Biddle & Reath LLP

(57) ABSTRACT

A laser processing method which can accurately cut an object to be processed along a line to cut is provided. A modified region 7 formed by multiphoton absorption forms a cutting start region 8 within an object to be processed 1 along a line 5 along which the object is intended to be cut. Thereafter, the object 1 is irradiated with laser light L2 transmittable through an unmodified region of the object 1, so as to generate fractures 24 from the cutting start region 8 acting as a start point, whereby the object 1 can accurately be cut along the line 5 along which the object is intended to be cut. Expanding an expandable film 19 having the object 1 secured thereto separates individual chips 25 from each other, which can further improve the reliability in cutting the object 1 along the line 5 along which the object is intended to be cut.

9 Claims, 17 Drawing Sheets

U.S. PATENT DOCUMENTS

| | | |
|---|---|---|
| 3,629,545 A | 12/1971 | Graham et al. |
| 3,790,051 A | 2/1974 | Moore |
| 3,790,744 A | 2/1974 | Bowen |
| 3,824,678 A | 7/1974 | Harris et al. |
| 3,970,819 A | 7/1976 | Gates et al. |
| 4,092,518 A | 5/1978 | Merard |
| 4,242,152 A | 12/1980 | Stone |
| 4,306,351 A | 12/1981 | Ohsaka et al. |
| 4,336,439 A | 6/1982 | Sasnett et al. |
| 4,475,027 A | 10/1984 | Pressley |
| 4,531,060 A | 7/1985 | Suwa et al. |
| 4,546,231 A | 10/1985 | Gresser et al. |
| 4,562,333 A | 12/1985 | Taub et al. |
| 4,650,619 A | 3/1987 | Watanabe |
| 4,682,003 A * | 7/1987 | Minakawa et al. ...... 219/121.72 |
| 4,734,550 A | 3/1988 | Imamura et al. |
| 4,769,310 A | 9/1988 | Gugger et al. |
| 4,814,575 A | 3/1989 | Petitbon |
| 4,899,126 A | 2/1990 | Yamada |
| 4,914,815 A | 4/1990 | Takada et al. |
| 4,981,525 A | 1/1991 | Kiyama et al. |
| 5,096,449 A * | 3/1992 | Matsuzaki ...................... 445/36 |
| 5,132,505 A * | 7/1992 | Zonneveld et al. ........ 219/121.6 |
| 5,211,805 A | 5/1993 | Srinivasan |
| 5,230,184 A | 7/1993 | Bkhman |
| 5,251,003 A | 10/1993 | Vigouroux et al. |
| 5,254,149 A | 10/1993 | Hashemi et al. |
| 5,254,833 A | 10/1993 | Okiyama |
| 5,304,357 A | 4/1994 | Sato et al. |
| 5,376,793 A * | 12/1994 | Lesniak ...................... 250/341.6 |
| 5,382,770 A | 1/1995 | Black et al. |
| 5,534,102 A | 7/1996 | Kadono et al. |
| 5,543,365 A * | 8/1996 | Wills et al. ................... 438/462 |
| 5,575,936 A | 11/1996 | Goldfarb |
| 5,580,473 A | 12/1996 | Shinohara et al. |
| 5,609,284 A | 3/1997 | Kondratenko |
| 5,622,540 A | 4/1997 | Stevens |
| 5,637,244 A | 6/1997 | Erokhin |
| 5,641,416 A | 6/1997 | Chadha |
| 5,656,186 A | 8/1997 | Mourou et al. |
| 5,767,483 A | 6/1998 | Cameron et al. |
| 5,776,220 A | 7/1998 | Allaire et al. |
| 5,786,560 A * | 7/1998 | Tatah et al. .............. 219/121.77 |
| 5,795,795 A | 8/1998 | Kousai et al. |
| 5,814,532 A | 9/1998 | Ichihara |
| 5,826,772 A | 10/1998 | Ariglio et al. |
| 5,841,543 A | 11/1998 | Guldi et al. |
| 5,882,956 A | 3/1999 | Umehara et al. |
| 5,886,319 A * | 3/1999 | Preston et al. ........... 219/121.72 |
| 5,900,582 A | 5/1999 | Tomita et al. |
| 5,925,271 A | 7/1999 | Pollack et al. |
| 5,968,382 A | 10/1999 | Matsumoto et al. |
| 5,976,392 A | 11/1999 | Chen |
| 5,998,238 A | 12/1999 | Kosaki |
| 6,031,201 A | 2/2000 | Amako et al. |
| 6,055,829 A | 5/2000 | Witzmann et al. |
| 6,057,525 A | 5/2000 | Chang et al. |
| 6,121,118 A | 9/2000 | Jin et al. |
| 6,127,005 A | 10/2000 | Lehman et al. |
| 6,156,030 A | 12/2000 | Neev |
| 6,172,329 B1 | 1/2001 | Shoemaker et al. |
| 6,175,096 B1 | 1/2001 | Nielsen |
| 6,181,728 B1 | 1/2001 | Cordingley et al. |
| 6,187,088 B1 | 2/2001 | Okumura |
| 6,211,488 B1 | 4/2001 | Hoekstra et al. |
| 6,229,114 B1 | 5/2001 | Andrews et al. |
| 6,252,197 B1 | 6/2001 | Hoekstra et al. |
| 6,257,224 B1 | 7/2001 | Yoshino et al. |
| 6,259,058 B1 | 7/2001 | Hockstra |
| 6,285,002 B1 | 9/2001 | Ngoi et al. |
| 6,294,439 B1 | 9/2001 | Sasaki et al. |
| 6,322,958 B1 | 11/2001 | Hayashi |
| 6,325,855 B1 | 12/2001 | Silmon et al. |
| 6,333,486 B1 * | 12/2001 | Troitski .................... 219/121.69 |
| 6,344,402 B1 | 2/2002 | Sekiya |
| 6,376,797 B1 | 4/2002 | Piwczyk et al. |
| 6,402,004 B1 | 6/2002 | Yoshikuni et al. |
| 6,407,363 B2 | 6/2002 | Dunsky et al. |
| 6,420,678 B1 | 7/2002 | Hockstra |
| 6,438,996 B1 | 8/2002 | Cuvelier |
| 6,489,588 B1 | 12/2002 | Hockstra et al. |
| 6,562,698 B2 * | 5/2003 | Manor .......................... 438/460 |
| 6,566,683 B1 | 5/2003 | Ogawa et al. |
| 6,653,210 B2 | 11/2003 | Choo et al. |
| 6,726,631 B2 | 4/2004 | Hatangadi et al. |
| 6,744,009 B1 | 6/2004 | Xuan et al. |
| 6,770,544 B2 | 8/2004 | Sawada |
| 6,787,732 B1 * | 9/2004 | Xuan et al. ................ 219/121.67 |
| 6,908,784 B1 | 6/2005 | Farnworth et al. |
| 6,951,799 B2 | 10/2005 | Roche |
| 6,992,026 B2 * | 1/2006 | Fukuyo et al. ................. 438/797 |
| 7,174,620 B2 * | 2/2007 | Chiba et al. ...................... 29/594 |
| 7,396,742 B2 | 7/2008 | Fukuyo et al. |
| 7,489,454 B2 | 2/2009 | Fukuyo et al. |
| 7,547,613 B2 | 6/2009 | Fukuyo et al. |
| 7,566,635 B2 | 7/2009 | Fujii et al. |
| 7,592,237 B2 | 9/2009 | Sakamoto et al. |
| 7,592,238 B2 | 9/2009 | Fukuyo et al. |
| 7,605,344 B2 | 10/2009 | Fukumitsu |
| 7,608,214 B2 | 10/2009 | Kuno et al. |
| 7,615,721 B2 | 11/2009 | Fukuyo et al. |
| 7,626,137 B2 | 12/2009 | Fukuyo et al. |
| 7,709,767 B2 | 5/2010 | Sakamoto |
| 7,718,510 B2 | 5/2010 | Sakamoto et al. |
| 7,719,017 B2 | 5/2010 | Tanaka |
| 7,732,730 B2 | 6/2010 | Fukuyo et al. |
| 7,749,867 B2 | 7/2010 | Fukuyo et al. |
| 7,754,583 B2 | 7/2010 | Sakamoto |
| 7,825,350 B2 | 11/2010 | Fukuyo et al. |
| 7,897,487 B2 | 3/2011 | Sugiura et al. |
| 7,902,636 B2 | 3/2011 | Sugiura et al. |
| 7,939,430 B2 | 5/2011 | Sakamoto et al. |
| 7,947,574 B2 | 5/2011 | Sakamoto et al. |
| 2001/0029673 A1 | 10/2001 | Brown et al. |
| 2001/0035401 A1 | 11/2001 | Manor |
| 2001/0046112 A1 | 11/2001 | Herchen |
| 2002/0006765 A1 | 1/2002 | Michel et al. |
| 2002/0025432 A1 | 2/2002 | Noguchi et al. |
| 2002/0096994 A1 | 7/2002 | Iwafuchi et al. |
| 2002/0115235 A1 | 8/2002 | Sawada |
| 2002/0158288 A1 | 10/2002 | Yamazaki et al. |
| 2002/0170896 A1 | 11/2002 | Choo et al. |
| 2002/0177288 A1 | 11/2002 | Brown et al. |
| 2003/0010275 A1 | 1/2003 | Radojevic et al. |
| 2003/0024909 A1 | 2/2003 | Hoekstra et al. |
| 2003/0141570 A1 | 7/2003 | Chen et al. |
| 2004/0002199 A1 | 1/2004 | Fukuyo et al. |
| 2004/0245659 A1 | 12/2004 | Glenn et al. |
| 2005/0173387 A1 | 8/2005 | Fukuyo et al. |
| 2005/0181581 A1 | 8/2005 | Fukuyo et al. |
| 2005/0184037 A1 | 8/2005 | Fukuyo et al. |
| 2005/0189330 A1 | 9/2005 | Fukuyo et al. |
| 2005/0194364 A1 | 9/2005 | Fukuyo et al. |
| 2005/0202596 A1 | 9/2005 | Fukuyo et al. |
| 2005/0272223 A1 | 12/2005 | Fujii et al. |
| 2006/0011593 A1 | 1/2006 | Fukuyo et al. |
| 2006/0040473 A1 | 2/2006 | Fukuyo et al. |
| 2006/0121697 A1 | 6/2006 | Fujii et al. |
| 2006/0144828 A1 | 7/2006 | Fukumitsu et al. |
| 2006/0148212 A1 | 7/2006 | Fukuyo et al. |
| 2006/0160331 A1 | 7/2006 | Fukuyo et al. |
| 2007/0085099 A1 | 4/2007 | Fukumitsu et al. |
| 2007/0125757 A1 | 6/2007 | Fukuyo et al. |
| 2007/0158314 A1 | 7/2007 | Fukumitsu et al. |
| 2007/0252154 A1 | 11/2007 | Uchiyama et al. |
| 2008/0035611 A1 | 2/2008 | Kuno et al. |
| 2008/0037003 A1 | 2/2008 | Atsumi et al. |
| 2008/0090382 A1 | 4/2008 | Fujii et al. |
| 2008/0218735 A1 | 9/2008 | Atsumi et al. |
| 2008/0251506 A1 | 10/2008 | Atsumi et al. |
| 2009/0008373 A1 | 1/2009 | Muramatsu et al. |
| 2009/0032509 A1 | 2/2009 | Kuno et al. |
| 2009/0098713 A1 | 4/2009 | Sakamoto |
| 2009/0107967 A1 | 4/2009 | Sakamoto et al. |
| 2009/0117712 A1 | 5/2009 | Sakamoto et al. |
| 2009/0166342 A1 | 7/2009 | Kuno et al. |
| 2009/0166808 A1 | 7/2009 | Sakamoto et al. |

| | | | | | | |
|---|---|---|---|---|---|---|
| 2009/0250446 | A1 | 10/2009 | Sakamoto | JP | 04-356942 | | 12/1992 |
| 2009/0261083 | A1 | 10/2009 | Osajima et al. | JP | 05-335726 | | 12/1993 |
| 2009/0302428 | A1 | 12/2009 | Sakamoto et al. | JP | 406039572 A * | 2/1994 |
| 2010/0006548 | A1 | 1/2010 | Atsumi et al. | JP | 06-188310 | | 7/1994 |
| 2010/0009547 | A1 | 1/2010 | Sakamoto | JP | 6-198475 | | 7/1994 |
| 2010/0012632 | A1 | 1/2010 | Sakamoto | JP | 07-029855 | | 1/1995 |
| 2010/0012633 | A1 | 1/2010 | Atsumi et al. | JP | 07-037840 | | 2/1995 |
| 2010/0015783 | A1 | 1/2010 | Fukuyo et al. | JP | 07-040336 | | 2/1995 |
| 2010/0025386 | A1 | 2/2010 | Kuno et al. | JP | 07-075955 A | 3/1995 |
| 2010/0032418 | A1 | 2/2010 | Kuno et al. | JP | 7-76167 | | 3/1995 |
| 2010/0055876 | A1 | 3/2010 | Fukuyo et al. | JP | 7-32281 | | 4/1995 |
| 2010/0151202 | A1 | 6/2010 | Fukumitsu | JP | 07-263382 | | 10/1995 |
| 2010/0176100 | A1 | 7/2010 | Fukuyo et al. | JP | 7-308791 | | 11/1995 |
| 2010/0184271 | A1 | 7/2010 | Sugiura et al. | JP | 8-148692 | | 6/1996 |
| 2010/0200550 | A1 | 8/2010 | Kumagai | JP | 8-197271 | | 8/1996 |
| 2010/0203678 | A1 | 8/2010 | Fukumitsu et al. | JP | 08-264488 | | 10/1996 |
| 2010/0203707 | A1 | 8/2010 | Fujii et al. | JP | 08-264491 | | 10/1996 |
| 2010/0227453 | A1 | 9/2010 | Sakamoto | JP | 09-017756 | | 1/1997 |
| 2010/0240159 | A1 | 9/2010 | Kumagai et al. | JP | 09-017831 | | 1/1997 |
| 2010/0258539 | A1 | 10/2010 | Sakamoto | JP | 9-150286 | | 6/1997 |
| 2010/0301521 | A1 | 12/2010 | Uchiyama | JP | 09-216085 A | 8/1997 |
| 2010/0311313 | A1 | 12/2010 | Uchiyama | JP | 9-260310 | | 10/1997 |
| 2010/0327416 | A1 | 12/2010 | Fukumitsu | JP | 09-263734 | | 10/1997 |
| 2011/0000897 | A1 | 1/2011 | Nakano et al. | JP | 10-034359 A | 2/1998 |
| 2011/0001220 | A1 | 1/2011 | Sugiura et al. | JP | 10-071483 | | 3/1998 |
| 2011/0021004 | A1 | 1/2011 | Fukuyo et al. | JP | 10-163780 | | 6/1998 |
| 2011/0027971 | A1 | 2/2011 | Fukuyo et al. | JP | 10-214997 | | 8/1998 |
| 2011/0027972 | A1 | 2/2011 | Fukuyo et al. | JP | 10-233373 | | 9/1998 |
| 2011/0037149 | A1 | 2/2011 | Fukuyo et al. | JP | 10-305420 | | 11/1998 |
| 2011/0274128 | A1 | 11/2011 | Fukumitsu et al. | JP | 10-321908 | | 12/1998 |
| | | | | JP | 11-028586 A | 2/1999 |

FOREIGN PATENT DOCUMENTS

| | | | | | | |
|---|---|---|---|---|---|---|
| DE | 196 46 332 | | 5/1998 | JP | 11-121517 | | 4/1999 |
| EP | 0345752 | A2 | 12/1989 | JP | 11-138896 | | 5/1999 |
| EP | 0 863 231 | A1 | 9/1998 | JP | 11-156564 | | 6/1999 |
| EP | 1 026 735 | A1 | 8/2000 | JP | 11-160667 | | 6/1999 |
| EP | 1 138 516 | | 10/2001 | JP | 11-162889 | | 6/1999 |
| EP | 1 498 216 | | 1/2005 | JP | 11-163097 | | 6/1999 |
| EP | 1 580 800 | | 9/2005 | JP | 11-163403 | | 6/1999 |
| JP | 46-24989 | | 7/1971 | JP | 11-177137 | | 7/1999 |
| JP | 48-12599 | | 2/1973 | JP | 11-177176 | | 7/1999 |
| JP | 53-33050 | | 3/1978 | JP | 11-207479 | | 8/1999 |
| JP | 53-141573 | | 12/1978 | JP | 11-221684 | | 8/1999 |
| JP | 56-076522 | | 6/1981 | JP | 11-224866 | | 8/1999 |
| JP | 56-028630 | | 7/1981 | JP | 11-267861 | | 10/1999 |
| JP | 56-128691 | | 10/1981 | JP | 11-071124 | | 11/1999 |
| JP | 58-36939 | | 3/1983 | JP | 2000-009991 | | 1/2000 |
| JP | 58-057767 | | 4/1983 | JP | 2000-015467 | | 1/2000 |
| JP | 58-171783 | | 10/1983 | JP | 2000-042764 | | 2/2000 |
| JP | 58-181492 | | 10/1983 | JP | 2000-61677 | | 2/2000 |
| JP | 59-76687 | | 5/1984 | JP | 2000-104040 | | 4/2000 |
| JP | 59-130438 | | 7/1984 | JP | 2000-124537 | | 4/2000 |
| JP | 59-141233 | | 8/1984 | JP | 2000-158156 | | 6/2000 |
| JP | 59-150691 | | 8/1984 | JP | 2000-195828 | | 7/2000 |
| JP | 60-55640 | | 3/1985 | JP | 2000-210785 | | 8/2000 |
| JP | 60-144985 | | 7/1985 | JP | 2000-216114 | | 8/2000 |
| JP | 60-167351 | | 8/1985 | JP | 2000-219528 | | 8/2000 |
| JP | 61-096439 | | 5/1986 | JP | 2000-237885 | | 9/2000 |
| JP | 61-112345 | | 5/1986 | JP | 2000-237886 | | 9/2000 |
| JP | 61-121453 | | 6/1986 | JP | 2000-247671 | | 9/2000 |
| JP | 61-220339 | | 9/1986 | JP | 02000249859 A * | 9/2000 |
| JP | 62-004341 | | 1/1987 | JP | 2000-323441 A | 11/2000 |
| JP | 62-098684 | A | 5/1987 | JP | 2001-47264 | | 2/2001 |
| JP | 63-215390 | | 9/1988 | JP | 2001-064029 | | 3/2001 |
| JP | 63-278692 | | 11/1988 | JP | 2001-085736 | | 3/2001 |
| JP | 64-038209 | | 2/1989 | JP | 2001-127015 | | 5/2001 |
| JP | 1-112130 | | 4/1989 | JP | 2001-135654 A | 5/2001 |
| JP | H1-225509 | | 9/1989 | JP | 2001-196282 | | 7/2001 |
| JP | H1-225510 | | 9/1989 | JP | 2001-250798 | | 9/2001 |
| JP | 03-124486 | | 5/1991 | JP | 2001-326194 | | 11/2001 |
| JP | 03-234043 | | 10/1991 | JP | 2001-345252 | | 12/2001 |
| JP | 3-276662 | | 12/1991 | JP | 2002-026443 | | 1/2002 |
| JP | 3-281073 | | 12/1991 | JP | 2002-47025 | | 2/2002 |
| JP | 04-029352 | | 1/1992 | JP | 2002-050589 | | 2/2002 |
| JP | 04-111800 | | 4/1992 | JP | 2002-158276 | | 5/2002 |
| JP | 04-167985 | | 6/1992 | JP | 2002-192367 | | 7/2002 |
| JP | 04-188847 | | 7/1992 | JP | 2002-192368 | | 7/2002 |
| JP | 4-300084 | | 10/1992 | JP | 2002-192369 | | 7/2002 |
| JP | 04-339586 | | 11/1992 | JP | 2002-192370 | | 7/2002 |
| | | | | JP | 2002-192371 | | 7/2002 |

| | | |
|---|---|---|
| JP | 2002-205180 | 7/2002 |
| JP | 2002-205181 | 7/2002 |
| JP | 2002205181 A * | 7/2002 |
| JP | 2002-224878 | 8/2002 |
| JP | 2002-226796 | 8/2002 |
| JP | 2003-001458 | 1/2003 |
| JP | 2003-017790 | 1/2003 |
| JP | 2003-039184 | 2/2003 |
| JP | 2003-046177 | 2/2003 |
| JP | 2003-154517 | 5/2003 |
| JP | 2003-334812 | 11/2003 |
| JP | 2003-338467 | 11/2003 |
| JP | 2003-338468 | 11/2003 |
| JP | 2003-338636 | 11/2003 |
| JP | 2005-001001 | 1/2005 |
| JP | 2005-047290 | 2/2005 |
| JP | 2005-159378 | 6/2005 |
| JP | 2005-159379 | 6/2005 |
| JP | 2005-313237 | 11/2005 |
| JP | 2006-128723 | 5/2006 |
| JP | 2006-135355 | 5/2006 |
| KR | 2001-017690 | 8/1999 |
| TW | 165354 | 8/1991 |
| TW | 192484 | 10/1992 |
| TW | 219906 | 2/1994 |
| TW | 404871 | 9/2000 |
| TW | 415036 | 12/2000 |
| TW | 428295 | 4/2001 |
| TW | 440551 | 6/2001 |
| TW | 443581 | 6/2001 |
| TW | 512451 | 12/2002 |
| TW | 521310 | 2/2003 |
| WO | WO 01/90709 A1 | 11/2001 |
| WO | WO 02/07927 A1 | 1/2002 |
| WO | WO 02/22301 | 3/2002 |
| WO | WO 03/076118 A1 | 9/2003 |
| WO | WO 2004/082006 | 9/2004 |

OTHER PUBLICATIONS

R. Sugiura et al., "The Stealth Dicing Technologies and Their Applications," Proceedings of the $63^{rd}$ Laser Materials Processing Conference, May 2005, pp. 115-123, with English Abstract.

T. Hidetsugu, "Stealth Dicing, Its Principles and Features: A Technology Most Suitable for Dicing Very Thin Semiconductor Wafers," Electronic Material No. 9, 2002, pp. 17-21, with English translation.

A. Ishii et al., CO2 Laser Processing Technology, Nikkan Kogyo Publishing Production, Dec. 21, 1992, pp. 63-65. w/partial English translation.

F. Fukuyo et al., "Stealth Dicing Technology for Ultra Thin Wafer", presented at 2003 ICEP (International Conference on Electronics Packaging), Apr. 16-18, 2003, Tokyo, Japan, pp. 266-269.

Journal of the Japan Society of Griding Engineers, vol. 47, No. 5, May 2003, pp. 229-231, English translation.

K. Hayashi, "Inner Glass Marking by Harmonics of Solid-state Laser", Proceedings of the $45^{th}$ Laser Materials Processing Conference, Dec. 1998, pp. 23-28, with English abstract.

K. Miura et al., "Formation of Photo-induced Structures in Glasses with Femtosecond Laser," Proceedings of $42^{nd}$ Laser Materials Processing Conference, Nov. 1997, pp. 105-111, with English abstract.

K. Midorikawa, "Recent Progress of Femtosecond Lasers and Their Applications to Material Processing", ISBN 4-947684-21-6, Dec. 1998, pp. 29-38, with English translation.

T. Miyazaki, "Laser Beam Machining Technology," Published by Sangyo-Tosho Inc., May 31, 1991, First Edition. pp. 9-10, with English translation.

T. Sano et al., "Evaluation of Processing Characteristics of Silicon With Picosecond Pulse Laser", Preprints of the National Meeting of Japan Welding Society, No. 66, Apr. 2000, pp. 72-73, w/English translation.

T. Yajima et al., New Version Laser Handbook, published by Asakusa Shoten, Jun. 15, 1989, pp. 666-669, with English translation.

The $6^{th}$ International Symposium on Laser Precision Microfabrication, Apr. 2005, Symposium Program and Technical Digest, including F. Fukuyo et al., "Stealth Dicing Technologies and Their Applications, Abstract."

Tooling Machine Series, Laser Machining, published by Taiga Shuppan, Inc., Sep. 10, 1990, pp. 91-96, with English translation.

U.S. Appl. No. 13/206,181, filed Aug. 9, 2011.
U.S. Appl. No. 13/269,274, filed Oct. 7, 2011.
U.S. Appl. No. 13/235,936, filed Sep. 19, 2011.
U.S. Appl. No. 13/213,175, filed Aug. 19, 2011.
U.S. Appl. No. 13/233,662, filed Sep. 15, 2011.
U.S. Appl. No. 13/061,438, filed Apr. 26, 2011.
U.S. Appl. No. 13/107,056, filed May 13, 2011.
U.S. Appl. No. 13/151,877, filed Jun. 2, 2011.
U.S. Appl. No. 13/131,429, filed Jun. 28, 2011.
U.S. Appl. No. 13/143,636, filed Sep. 21, 2011.
U.S. Appl. No. 13/148,097, filed Aug. 26, 2011.
U.S. Appl. No. 13/262,995, filed Oct. 5, 2011.
U.S. Appl. No. 13/265,027, filed Oct. 18, 2011.

X. Liu et al., "Laser Ablation and Micromachining with Ultrashort Laser Pulses," IEEE Journal of Quantum Electronics, vol. 33, No. 10, Oct. 1997, pp. 1706-1716.

Office Action dated Apr. 25, 2012 from related (not counterpart) U.S. Appl. No. 12/912,427 (33 pages).

* cited by examiner

LASER BEAM MACHINING METHOD

TECHNICAL FIELD

The present invention relates to a laser processing method used for cutting an object to be processed such as semiconductor material substrate, piezoelectric material substrate, or glass substrate.

BACKGROUND ART

An example of literatures disclosing a conventional technique of this kind is International Publication Pamphlet No. 02/22301. The specification of this literature discloses a technique of irradiating an object to be processed with laser light, so as to form a modified region within the object along a line along which the object is intended to be cut, and cutting the object from the modified region acting as a start point.

DISCLOSURE OF THE INVENTION

Since the technique disclosed in the above-mentioned literature is a quite effective technique which can accurately cut the object along a line along which the object is intended to be cut, there has been a demand for a technique which can cut the object from the modified region more accurately.

In view of such circumstances, it is an object of the present invention to provide a laser processing method which can accurately cut the object from the line along which the object is intended to be cut.

In order to achieve the above-mentioned object, in one aspect, the present invention provides a laser processing method comprising a first step of irradiating a wafer-like object to be processed with laser light while locating a light-converging point within the object, so as to form a modified region due to multiphoton absorption within the object, and causing the modified region to form a cutting start region inside of a laser light entrance surface of the object by a predetermined distance along a line along which the object is intended to be cut in the object; and a second step of irradiating the modified region with laser light transmittable through an unmodified region of the object and more absorbable by the modified region than by the unmodified region after the first step, so as to generate a stress at a portion where the object is cut along the line along which the object is intended to be cut.

This laser processing method forms a modified region within an object to be processed by irradiating the object with laser light while locating a light-converging point within the object and utilizing a phenomenon of multiphoton absorption in the first step. When a start point exists at a portion where the object is to be cut, the object can be cleaved with a relatively small force, so as to be cut. This laser processing method irradiates the object with laser light transmittable through an unmodified region of the object and more absorbable by the modified region than by the unmodified region along a line along which the object is intended to be cut in the second step, so that the object is heated along the modified region, whereby a stress such as thermal stress due to a temperature difference occurs. This stress grows a crack in the thickness direction of the object from the modified region acting as a start point, thereby making it possible to cleave and cut the object. Thus, the object can be cut by a relatively small force such as a stress typified by a thermal stress due to a temperature difference, whereby the object can be cut with a high accuracy without generating unnecessary fractures deviating from the line along which the object is intended to be cut on a surface of the object.

This laser processing method forms the modified region by locally generating multiphoton absorption within the object in the first step. In the second step, laser light transmittable through the unmodified region is emitted. Therefore, the laser light is hardly absorbed at the surface of the object, so that the surface of the object is hardly molten in both steps. The unmodified region refers to a region not formed with a modified region after the first step. The light-converging point refers to a portion where the laser light is converged. The line along which the object is intended to be cut may be a line actually drawn on the surface of the object or therewithin, or a virtual line.

In another aspect, the present invention provides a laser processing method comprising a first step of irradiating a wafer-like object to be processed with laser light while locating a light-converging point within the object under a condition with a peak power density of at least $1 \times 10^8$ (W/cm$^2$) at the light-converging point and a pulse width of 1 μs or less, so as to form a modified region including a crack region within the object, and causing the modified region to form a cutting start region inside of a laser light entrance surface of the object by a predetermined distance along a line along which the object is intended to be cut in the object; and a second step of irradiating the modified region with laser light transmittable through an unmodified region of the object and more absorbable by the modified region than by the unmodified region after the first step, so as to generate a stress at a portion where the object is cut along the line along which the object is intended to be cut.

This laser processing method irradiates the object with laser light while locating a light-converging point within the object under a condition with a peak power density of at least $1 \times 10^8$ (W/cm$^2$) at the light-converging point and a pulse width of 1 μs or less in the first step. Consequently, a phenomenon of optical damage due to multiphoton absorption occurs within the object. This optical damage induces a thermal distortion within the object, thereby forming a crack region therewithin. Since this crack region is an example of the above-mentioned modified region while the second step is equivalent to that mentioned above, this laser processing method enables laser processing without melting the surface of the object or generating unnecessary fractures thereon deviating from the line along which the object is intended to be cut. An example of the object to be processed in this laser processing method is a member including glass. The peak power density refers to the electric field intensity at the light-converging point of pulsed laser light.

In still another aspect, the present invention provides a laser processing method comprising a first step of irradiating a wafer-like object to be processed with laser light while locating a light-converging point within the object under a condition with a peak power density of at least $1 \times 10^8$ (W/cm$^2$) at the light-converging point and a pulse width of 1 μs or less, so as to form a modified region including a molten processed region within the object, and causing the modified region to form a cutting start region inside of a laser light entrance surface of the object by a predetermined distance along a line along which the object is intended to be cut in the object; and a second step of irradiating the modified region with laser light transmittable through an unmodified region of the object and more absorbable by the modified region than by the unmodified region after the first step, so as to generate a stress at a portion where the object is cut along the line along which the object is intended to be cut.

This laser processing method irradiates the object with laser light while locating a light-converging point within the object under a condition with a peak power density of at least $1 \times 10^8$ (W/cm$^2$) at the light-converging point and a pulse width of 1 μs or less in the first step. Consequently, the inside of the object is locally heated by multiphoton absorption. The heating forms a molten processed region within the object. Since this molten processed region is an example of the above-mentioned modified region while the second step is equivalent to that mentioned above, this laser processing method enables laser processing without melting the surface of the object or generating unnecessary fractures thereon deviating from the line along which the object is intended to be cut. An example of the object to be processed in this laser processing method is a member including a semiconductor material.

In still another aspect, the present invention provides a laser processing method comprising a first step of irradiating a wafer-like object to be processed with laser light while locating a light-converging point within the object under a condition with a peak power density of at least $1 \times 10^8$ (W/cm$^2$) at the light-converging point and a pulse width of 1 ns or less, so as to form a modified region including a refractive index change region as a region with a changed refractive index within the object, and causing the modified region to form a cutting start region inside of a laser light entrance surface of the object by a predetermined distance along a line along which the object is intended to be cut in the object; and a second step of irradiating the modified region with laser light transmittable through an unmodified region of the object and more absorbable by the modified region than by the unmodified region after the first step, so as to generate a stress at a portion where the object is cut along the line along which the object is intended to be cut.

This laser processing method irradiates the object with laser light while locating a light-converging point within the object under a condition with a peak power density of at least $1 \times 10^8$ (W/cm$^2$) at the light-converging point and a pulse width of 1 ns or less. When multiphoton absorption is thus generated within the object with a very short pulse width, the energy due to the multiphoton absorption is not converted into thermal energy, whereas an eternal structural change such as ionic valence change, crystallization, or polarization orientation is induced within the object, whereby a refractive index change region is formed. Since the refractive index change region is an example of the above-mentioned modified region while the second step is equivalent to that mentioned above, this laser processing method enables laser processing without melting the surface of the object or generating unnecessary fractures thereon deviating from the line along which the object is intended to be cut. An example of the object to be processed in this laser processing method is a member including glass.

Preferably, the second step performs the same laser light irradiation as with the first step while locating a light-converging point at the modified region. Even when the second step performs the same laser light irradiation as with the first step, the laser light absorption due to scattering by the modified region, changes in physical properties of the modified region, etc. or the occurrence of multiphoton absorption in the modified region can heat the object along the modified region without melting the front face of the object, thereby generating a stress such as thermal stress due to a temperature difference.

In still another aspect, the present invention provides a laser processing method comprising the steps of irradiating a wafer-like object to be processed secured to a surface of an expandable holding member with laser light while locating a light-converging point within the object, so as to form a modified region within the object, and causing the modified region to form a cutting start region inside of a laser light entrance surface of the object by a predetermined distance along a line along which the object is intended to be cut in the object; irradiating the modified region with laser light transmittable through an unmodified region of the object after the step of forming the cutting start region, so as to cut the object along the line along which the object is intended to be cut; and expanding the holding member after the step of cutting the object, so as to separate cut portions of the object from each other.

In this laser processing method, the modified region formed by multiphoton absorption can form a cutting start region within the object along a desirable line along which the object is intended to be cut the object. Then, irradiating the object with laser light transmittable through the unmodified region (the part of the object other than the modified region) along the line along which the object is intended to be cut can generate fractures from the cutting start region acting as a start point, whereby the object can be cut accurately along the line along which the object is intended to be cut. Expanding the holding member having the object secured thereto separates portions of the object from each other, whereby the reliability in cutting the object along the line along which the object is intended to be cut can further be improved.

In still another aspect, the present invention provides a laser processing method comprising the steps of irradiating a wafer-like object to be processed secured to a surface of an expandable holding member with laser light while locating a light-converging point within the object, so as to form a modified region within the object, and causing the modified region to form a cutting start region inside of a laser light entrance surface of the object by a predetermined distance along a line along which the object is intended to be cut in the object; irradiating the modified region with laser light transmittable through an unmodified region of the object after the step of forming the cutting start region; and expanding the holding member after the step of irradiating the object, so as to cut the object and separate cut portions of the object from each other.

This laser processing method can form a cutting start region within the object along a line along which the object is intended to be cut as with the laser processing methods mentioned above. Then, irradiating the object with laser light transmittable through the unmodified region along a line along which the object is intended to be cut allows fractures started from the cutting start region to reach the front and rear faces of the object with a smaller force than that in the case without such irradiation. Therefore, the holding member having the object secured thereto can be expanded with a smaller force, so that the object can be cut accurately. Expanding the holding member separates portions of the object from each other, so that the reliability in cutting the object along the line along which the object is intended to be cut can further be improved.

The cutting start region refers to a region to become a start point for cutting when cutting the object. Therefore, the cutting start region is a part to cut where cutting is to be done in the object. The cutting start region may be made by a modified region formed continuously or modified regions formed intermittently. The object may be formed from a semiconductor material, in which the modified region is a molten processed region.

BEST MODES FOR CARRYING OUT THE INVENTION

In the following, a preferred embodiment of the present invention will be explained in detail with reference to the drawings. The laser processing method in accordance with this embodiment forms a modified region by utilizing multiphoton absorption. The multiphoton absorption is a phenomenon occurring when the intensity of laser light is very high. Therefore, the multiphoton absorption will be explained first in brief.

A material becomes transparent when its absorption bandgap $E_G$ is greater than photon energy hv. Hence, a condition under which absorption occurs in the material is hv>$E_G$. However, even when optically transparent, the material generates absorption under a condition of nhv>$E_G$ (where n=2, 3, 4, . . . ) if the intensity of laser light becomes very high. This phenomenon is known as multiphoton absorption. In the case of pulsed waves, the intensity of laser light is determined by the peak power density (W/cm$^2$) of laser light at a light-converging point. The multiphoton absorption occurs under a condition where the peak power density is 1×10$^8$ (W/cm$^2$) or greater, for example. The peak power density is determined by (energy of laser light at the light-converging point per pulse)/(beam spot cross-sectional area of laser light×pulse width). In the case of continuous waves, the intensity of laser light is determined by the field intensity (W/cm$^2$) of laser light at the light-converging point.

Figure 1:
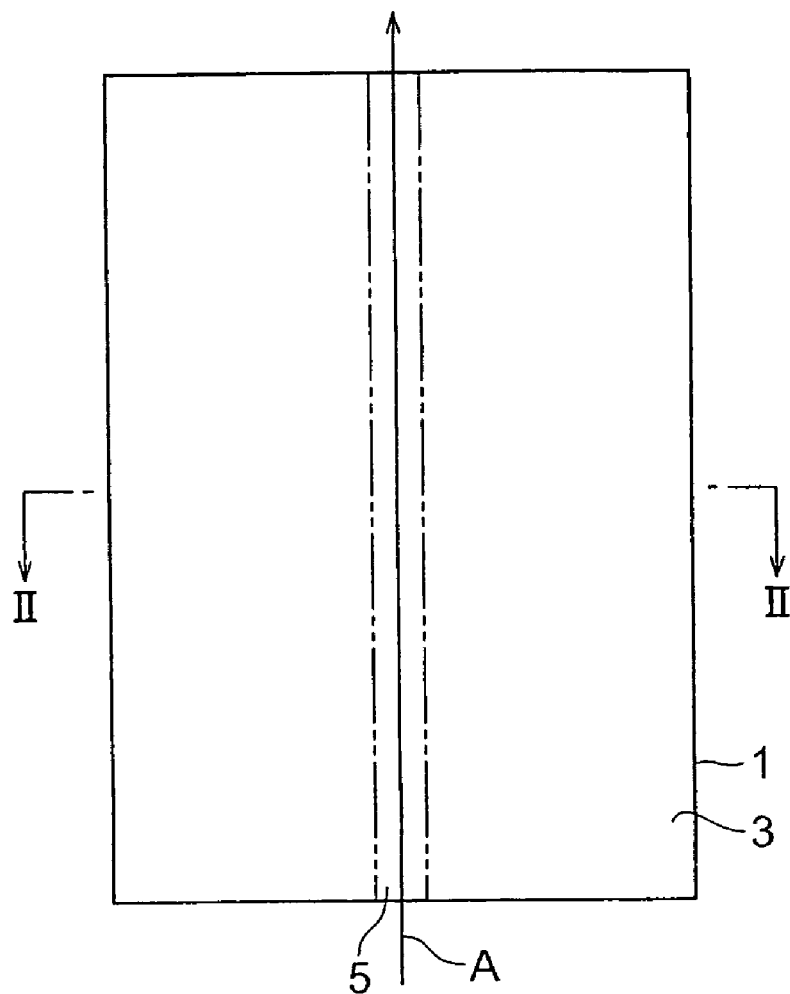
FIG. 1 is a plan view of an object to be processed during laser processing by the laser processing method in accordance with an embodiment.
Figure 2:
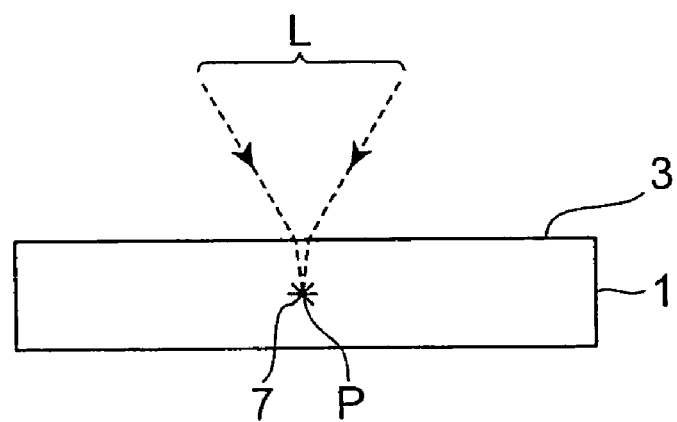
FIG. 2 is a sectional view of the object taken along the line II-II of FIG. 1.
Figure 3:
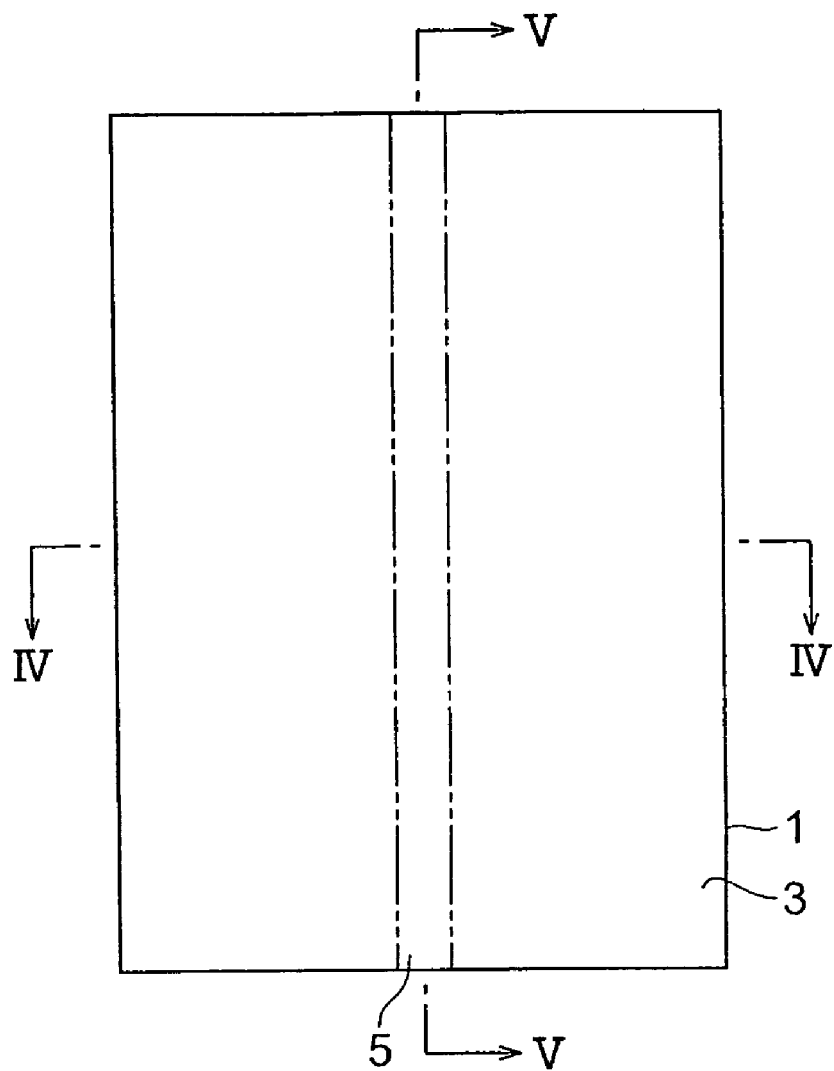
FIG. 3 is a plan view of the object after the laser processing by the laser processing method in accordance with the embodiment.
Figure 4:
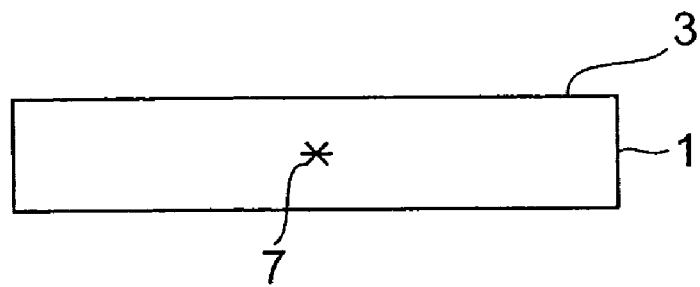
FIG. 4 is a sectional view of the object taken along the line IV-IV of FIG. 3.
Figure 5:
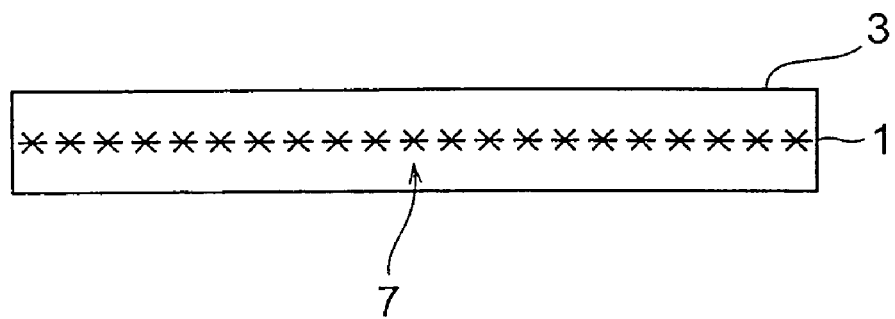
FIG. 5 is a sectional view of the object taken along the line V-V of FIG. 3.
Figure 6:
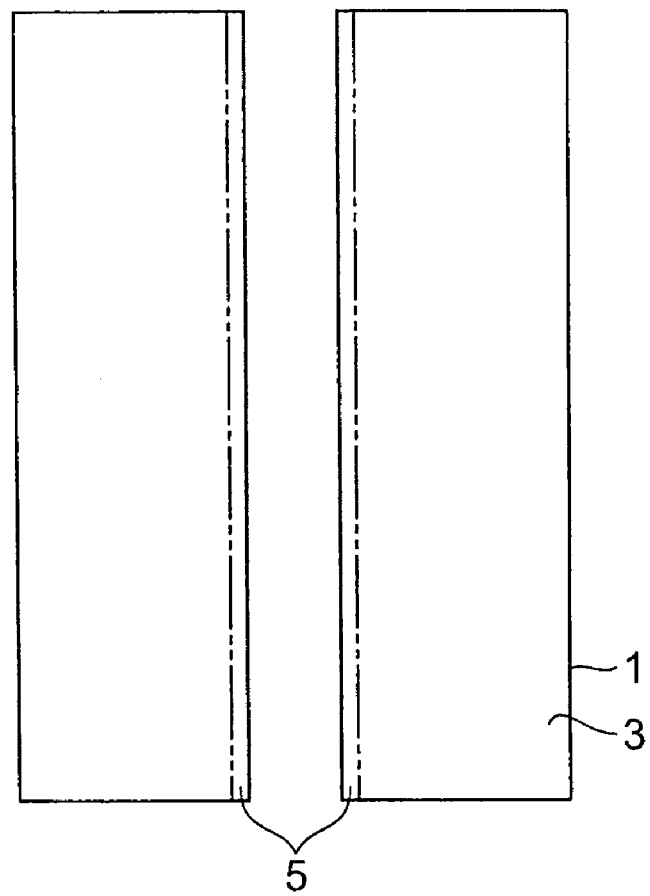
FIG. 6 is a plan view of the object cut by the laser processing method in accordance with the embodiment.

The principle of the laser processing method in accordance with the embodiment using such multiphoton absorption will be explained with reference to FIGS. 1 to 6. FIG. 1 is a plan view of an object to be processed 1 during laser processing. FIG. 2 is a sectional view of the object 1 taken along the line II-II of FIG. 1. FIG. 3 is a plan view of the object 1 after the laser processing. FIG. 4 is a sectional view of the object 1 taken along the line IV-IV of FIG. 3. FIG. 5 is a sectional view of the object 1 taken along the line V-V of FIG. 3. FIG. 6 is a plan view of the cut object 1.

As shown in FIGS. 1 and 2, a line 5 along which the object is intended to be cut exists on a front face 3 of the object 1. The line 5 along which the object is intended to be cut is a virtual line extending straight. The laser processing in accordance with this embodiment irradiates the object 1 with laser light L while locating a light-converging point P within the object 1 under a condition generating multiphoton absorption, so as to form a modified region 7. The light-converging point P is a position at which the laser light L is converged.

The laser light L is relatively moved along the line 5 along which the object is intended to be cut (i.e., in the direction of arrow A), so as to shift the light-converging point P along the line 5 along which the object is intended to be cut. Consequently, as shown in FIGS. 3 to 5, the modified region 7 is formed along the line 5 along which the object is intended to be cut only within the object 1. In the laser processing method in accordance with this embodiment, the modified region 7 is not formed by the heat generated from the object 1 absorbing the laser light L. The laser light L is transmitted through the object 1, so as to generate multiphoton absorption therewithin, thereby forming the modified region 7. Therefore, the front face 3 of the object 1 hardly absorbs the laser light L and does not melt.

When a start point exists in a portion to cut at the time of cutting the object 1, the object 1 fractures from the start point, whereby the object 1 can be cut with a relatively small force as shown in FIG. 6. Therefore, the object 1 can be cut without generating unnecessary fractures on the front face 3 of the object 1.

There seem to be the following two ways of cutting an object to be processed from the modified region acting as the start point. The first case is where an artificial force is applied to the object after forming the modified region, so that the object fractures from the modified region, whereby the object is cut. This is the cutting in the case where the object has a large thickness, for example. Applying an artificial force refers to exerting a bending stress or shear stress to the object along the cutting start region, or generating a thermal stress by applying a temperature difference to the object, for example. The other case is where the forming of the modified region causes the object to fracture naturally in its cross-sectional direction (thickness direction) from the modified region acting as a start point, thereby cutting the object. This becomes possible, for example, if one modified region is formed when the object 1 has a small thickness, or if a plurality of modified regions are formed in the thickness direction when the object has a large thickness. Even in this naturally fracturing case, fractures do not extend onto the front face at a portion corresponding to an area not formed with the modified region, so that only the portion corresponding to the area formed with the modified region can be cleaved, whereby cleavage can be controlled well. Such a cleaving method with a favorable controllability is quite effective, since the object such as silicon wafer has recently been apt to decrease its thickness.

The modified region formed by multiphoton absorption in this embodiment encompasses the following cases (1) to (3):

(1) Case where the Modified Region is a Crack Region Including One Crack or a Plurality of Cracks An object to be processed (e.g., glass or a piezoelectric material made of $LiTaO_3$) is irradiated with laser light while locating a light-converging point therewithin under a condition with a field intensity of at least $1 \times 10^8$ (W/cm$^2$) at the light-converging point and a pulse width of 1 μs or less. This magnitude of pulse width is a condition under which a crack region can be formed only within the object while generating multiphoton absorption without causing unnecessary damages to the object. This generates a phenomenon of optical damage by multiphoton absorption within the object. This optical damage induces a thermal distortion within the object, thereby forming a crack region therewithin. The upper limit of field intensity is $1 \times 10^{12}$ (W/cm$^2$), for example. The pulse width is preferably 1 ns to 200 ns, for example. The forming of a crack region by multiphoton absorption is disclosed, for example, in "Internal Marking of Glass Substrate with Solid-state Laser Harmonics", Proceedings of the 45th Laser Materials Processing Conference (December, 1998), pp. 23-28.

The inventors determined the relationship between field intensity and crack size by an experiment. The following are conditions of the experiment.

(A) Object to be processed: Pyrex (registered trademark) glass (with a thickness of 700 μm and an outer diameter of 4 inches)

(B) Laser
light source: semiconductor laser pumping Nd:YAG laser
wavelength: 1064 nm
laser light spot cross-sectional area: $3.14 \times 10^{-8}$ cm$^2$
oscillation mode: Q-switched pulse
repetition frequency: 100 kHz
pulse width: 30 ns
output: output<1 mJ/pulse
laser light quality: $TEM_{00}$
polarizing property: linear polarization (C) Condenser lens
transmittance at a laser light wavelength: 60%

(D) Moving rate of the mounting table mounting the object: 100 mm/sec

The laser light quality of $TEM_{00}$ means that the light-converging characteristic is so high that convergence to about the wavelength of laser light is possible.

Figure 7:
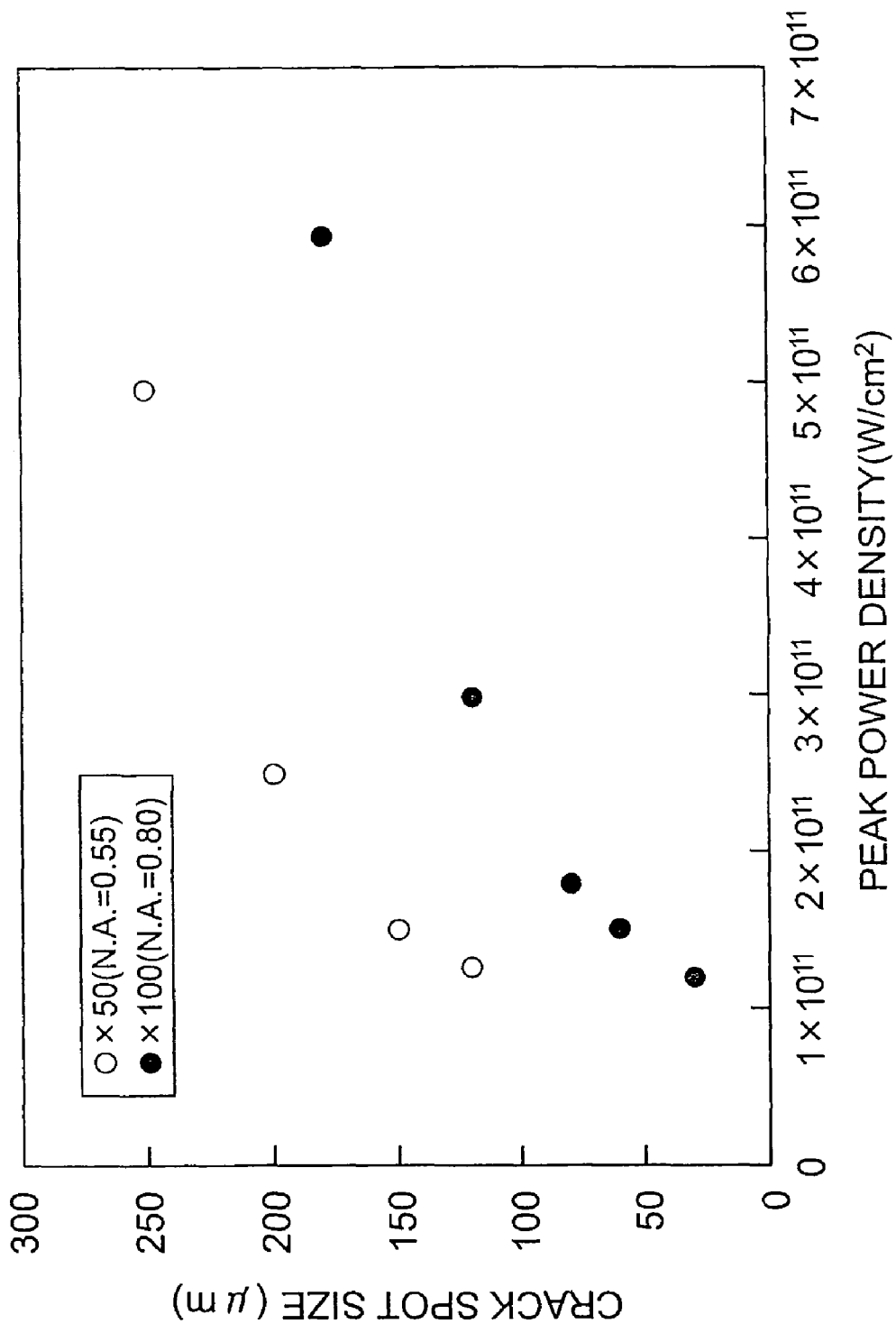
FIG. 7 is a graph showing relationships between the field intensity and crack spot size in the laser processing method in accordance with the embodiment.

FIG. 7 is a graph showing the results of the above-mentioned experiment. The abscissa indicates the peak power density. Since the laser light is pulsed laser light, the field intensity is represented by the peak power density. The ordinate indicates the size of a crack spot formed within the object by one pulse of laser light. The crack spot size is the size of a part yielding the maximum length among forms of crack spots. Data represented by black circles in the graph refer to a case where the condenser lens (C) has a magnification of ×100 and a numerical aperture (NA) of 0.80. On the other hand, data represented by whitened circles in the graph refer to a case where the condenser lens (C) has a magnification of ×50 and a numerical aperture (NA) of 0.55. Crack spots are seen to occur within the object from when the peak power density is about $10^{11}$ (W/cm$^2$) and become greater as the peak power density increases.

Figure 8:
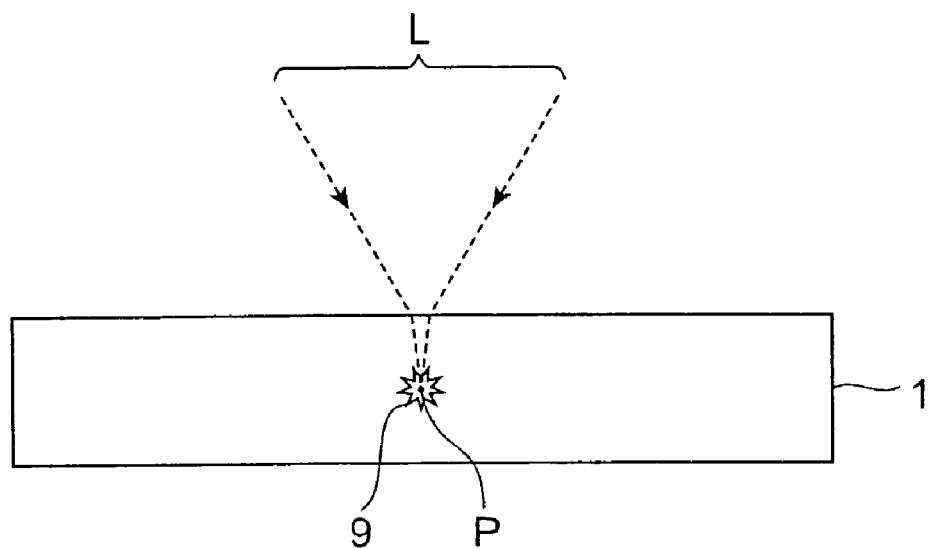
FIG. 8 is a sectional view of the object in a first step of the laser processing method in accordance with the embodiment.
Figure 9:
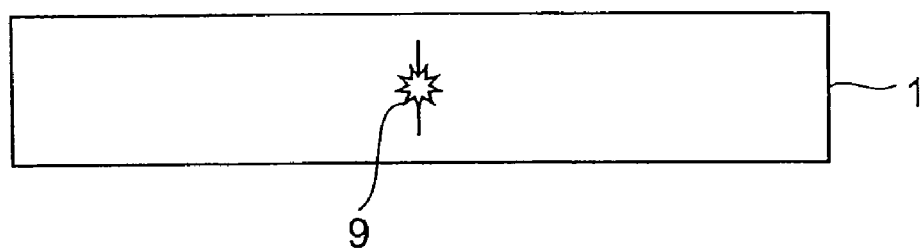
FIG. 9 is a sectional view of the object in a second step of the laser processing method in accordance with the embodiment.
Figure 10:
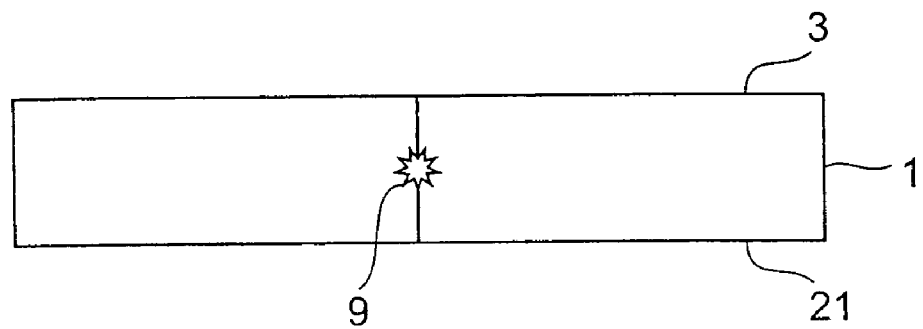
FIG. 10 is a sectional view of the object in a third step of the laser processing method in accordance with the embodiment.
Figure 11:
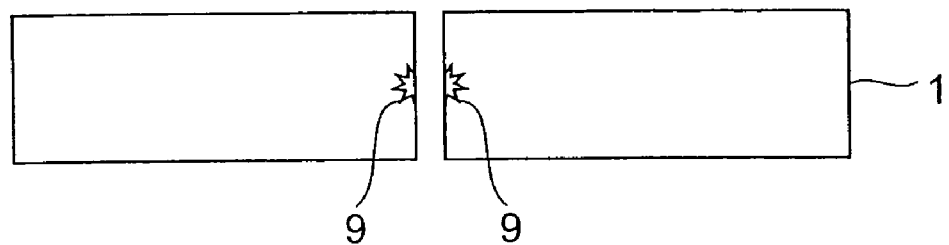
FIG. 11 is a sectional view of the object in a fourth step of the laser processing method in accordance with the embodiment.

A mechanism by which the objet to be processed is cut by forming a crack region will now be explained with reference to FIGS. 8 to 11. As shown in FIG. 8, the object 1 is irradiated with laser light L while the light-converging point P is located within the object 1 under a condition where multiphoton absorption occurs, so as to form a crack region 9 therewithin along a line to cut. The crack region 9 is a region containing one crack or a plurality of cracks. A crack further grows from the crack region 9 acting as a start point as shown in FIG. 9, and reaches the front face 3 and rear face 21 of the object 1 as shown in FIG. 10, whereby the object 1 fractures and is consequently cut as shown in FIG. 11. The crack reaching the front and rear faces of the object may grow naturally or as a force is applied to the object.

(2) Case where the Modified Region is a Molten Processed Region

An object to be processed (e.g., semiconductor material such as silicon) is irradiated with laser light while locating a light-converging point within the object under a condition with a field intensity of at least $1 \times 10^8$ (W/cm$^2$) at the light-converging point and a pulse width of 1 μs or less. As a consequence, the inside of the object is locally heated by multiphoton absorption. This heating forms a molten processed region within the object. The molten processed region encompasses regions once molten and then re-solidified, regions just in a molten state, and regions in the process of being re-solidified from the molten state, and can also be referred to as a region whose phase has changed or a region whose crystal structure has changed. The molten processed region may also be referred to as a region in which a certain structure has changed to another structure among monocrystal, amorphous, and polycrystal structures. For example, it means a region having changed from the monocrystal structure to the amorphous structure, a region having changed from the monocrystal structure to the polycrystal structure, or a region having changed from the monocrystal structure to a structure containing amorphous and polycrystal structures. When the object to be processed is of a silicon monocrystal structure, the molten processed region is an amorphous silicon structure, for example. The upper limit of field intensity is $1 \times 10^{12}$ (W/cm$^2$), for example. The pulse width is preferably 1 ns to 200 ns, for example.

By an experiment, the inventors verified that a molten processed region was formed within a silicon wafer. The following are conditions of the experiment.

(A) Object to be processed: silicon wafer (with a thickness of 350 μm and an outer diameter of 4 inches)

(B) Laser light source: semiconductor laser pumping Nd:YAG laser wavelength: 1064 nm laser light spot cross-sectional area: $3.14 \times 10^{-8}$ cm$^2$ oscillation mode: Q-switched pulse repetition frequency: 100 kHz pulse width: 30 ns output: 20 μJ/pulse laser light quality: TEM$_{00}$ polarizing property: linear polarization (C) Condenser lens magnification: ×50

N.A.: 0.55 transmittance at a laser light wavelength: 60%

(D) Moving rate of the mounting table mounting the object: 100 mm/sec

Figure 12:
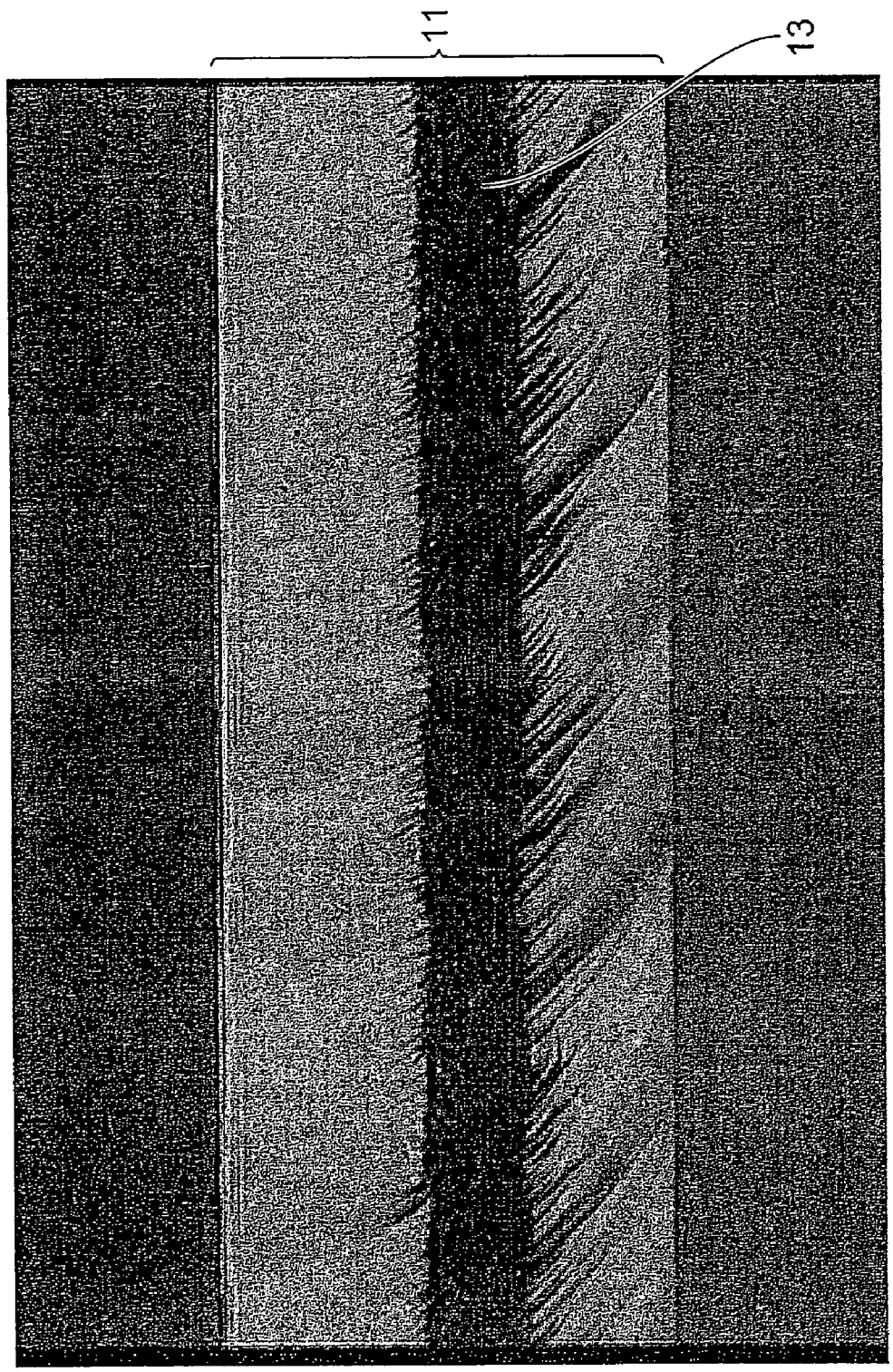
FIG. 12 is a view showing a photograph of a cross section of a part of a silicon wafer cut by the laser processing method in accordance with the embodiment.

FIG. 12 is a view showing a photograph of a cross section of a part of a silicon wafer cut by laser processing under the conditions mentioned above. A molten processed region 13 is formed within the silicon wafer 11. The molten processed region 13 formed under the above-mentioned conditions has a size of about 100 μm in the thickness direction.

Figure 13:
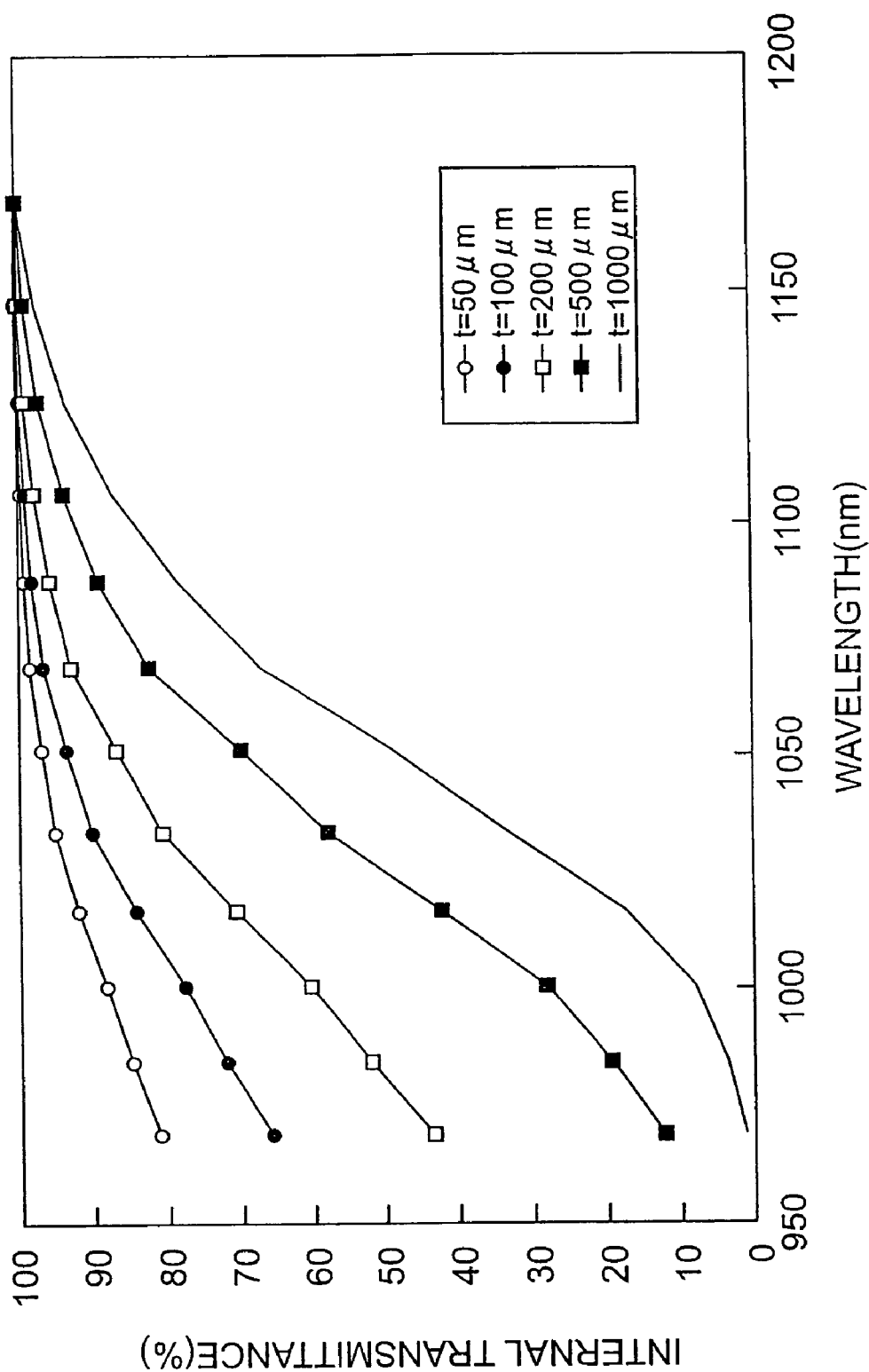
FIG. 13 is a graph showing relationships between the laser light wavelength and the transmittance within the silicon substrate in the laser processing method in accordance with the embodiment.

The fact that the molten processed region 13 is formed by multiphoton absorption will now be explained. FIG. 13 is a graph showing relationships between the laser light wavelength and the transmittance within the silicon substrate. Here, the respective reflected components on the front and rear sides of the silicon substrate are eliminated, so as to show the internal transmittance alone. The respective relationships are shown in the cases where the thickness t of the silicon substrate is 50 μm, 100 μm, 200 μm, 500 μm, and 1000 μm.

For example, at the Nd:YAG laser wavelength of 1064 nm, the laser light appears to be transmitted through the silicon substrate by at least 80% when the silicon substrate has a thickness of 500 μm or less. Since the silicon wafer 11 shown in FIG. 12 has a thickness of 350 μm, the molten processed region 13 caused by multiphoton absorption is formed near the center of the silicon wafer 11, i.e., at a part distanced from the front face by 175 μm. The transmittance in this case is 90% or more with reference to a silicon wafer having a thickness of 200 μm, whereby the laser light is absorbed only slightly within the silicon wafer 11 but is substantially transmitted therethrough. This means that the molten processed region 13 is formed within the silicon wafer 11 not by laser light absorption within the silicon wafer 11 (i.e., not by usual heating with the laser light) but by multiphoton absorption. The forming of a molten processed region by multiphoton absorption is disclosed, for example, in "Silicon Processing Characteristic Evaluation by Picosecond Pulse Laser", Preprints of the National Meetings of Japan Welding Society, Vol. 66 (April, 2000), pp. 72-73.

A fracture is generated in a silicon wafer from a cutting start region formed by a molten processed region, acting as a start point, toward a cross section, and reaches the front and rear faces of the silicon wafer, whereby the silicon wafer is cut. The fracture reaching the front and rear faces of the silicon wafer may grow naturally or as a force is applied to the object. The fracture naturally growing from the cutting start region to the front and rear faces of the wafer encompasses a case where the fracture grows from a state where the molten processed region forming the cutting start region is molten and a case where the fracture grows when the molten processed region forming the cutting start region is re-solidified from the molten state. In either case, the molten processed region is formed only within the wafer, and thus is present only within the cross section after cutting as shown in FIG. 12. When the molten processed region is formed within the object, unnecessary fractures deviating from a line to cut are harder to occur at the time of cleaving, whereby cleavage control becomes easier.

(3) Case where the Modified Region is a Refractive Index Change Region

An object to be processed (e.g., glass) is irradiated with laser light while locating a light-converging point within the object under a condition with a field intensity of at least $1 \times 10^8$ (W/cm$^2$) at the light-converging point and a pulse width of 1 ns or less. When multiphoton absorption is generated within the object with a very short pulse width, the energy caused by multiphoton absorption is not converted into thermal energy, whereby an eternal structure change such as ion valence change, crystallization, or orientation polarization is induced within the object, thus forming a refractive index change region. The upper limit of field intensity is $1 \times 10^{12}$ (W/cm$^2$), for example. The pulse width is preferably 1 ns or less, for example, more preferably 1 ps or less. The forming of a refractive index change region by multiphoton absorption is disclosed, for example, in "Forming of Photoinduced Structure within Glass by Femtosecond Laser Irradiation", Proceedings of the 42nd Laser Materials Processing Conference (November 1997), pp. 105-111.

In the above, cases (1) to (3) are explained as a modified region formed due to multiphoton absorption within the object, but when under the consideration of crystal structure and cleave of a wafer type object to be processed, cutting start region is formed as stated below, it is possible to cut a object to be processed with smaller power and higher accuracy by using the cutting start region as a start point of the object.

That is, in the case that the object to be processed is a substrate made of a single crystal semiconductor having a diamond structure such as a silicon, it is preferable to form a cutting start region in a direction along (1, 1, 1) (the first cleavage plane) or (1, 1, 0) plane (the second cleavage plane) of the object in the object. Further, in the case that the object to be processed is a substrate made of III-V group compound semiconductor having a blende type crystal structure such as a GaAs, it is preferable to form a cutting start region in a direction along (1, 1, 0) plane of the object in the object. More further, in the case that the object to be processed is a substrate having a hexagonal type crystal structure such as Safire (Al$_2$O$_3$), it is preferable to form a cutting start region in a direction along (1, 1, 2, 0) plane (A plane) or (1, 1, 0, 0) plane (M plane) of the object in the object when a main surface of the object is (0, 0, 0, 1) plane (C plane).

Besides, when an orientation flat is formed in the substrate along the above stated direction along which the above explained cutting start region should be formed in the object, for example a direction along (1, 1, 1) plane in the single crystal silicon substrate) or along a direction perpendicular to the direction along which the above explained cutting start region should be formed in the object, it is possible to form the cutting start region along the direction along which the cutting start region should be formed in the object in the object with easy and high accuracy by using the orientation flat as a reference.

The invention will be explained concretely, referring embodiments hereinbelow.

Example 1

Example 1 of the present invention will now be explained. The laser processing method in accordance with Example 1 comprises a modified region forming step (first step) of forming a modified region due to multiphoton absorption within an object to be processed, and a stress step (second step) of generating a stress in a portion to cut the object. In Example 1, the modified region forming step and stress step perform the same laser light irradiation. Therefore, a laser processing apparatus which will be explained later emits laser light twice under the same condition in the modified region forming step and stress step.

Figure 14:
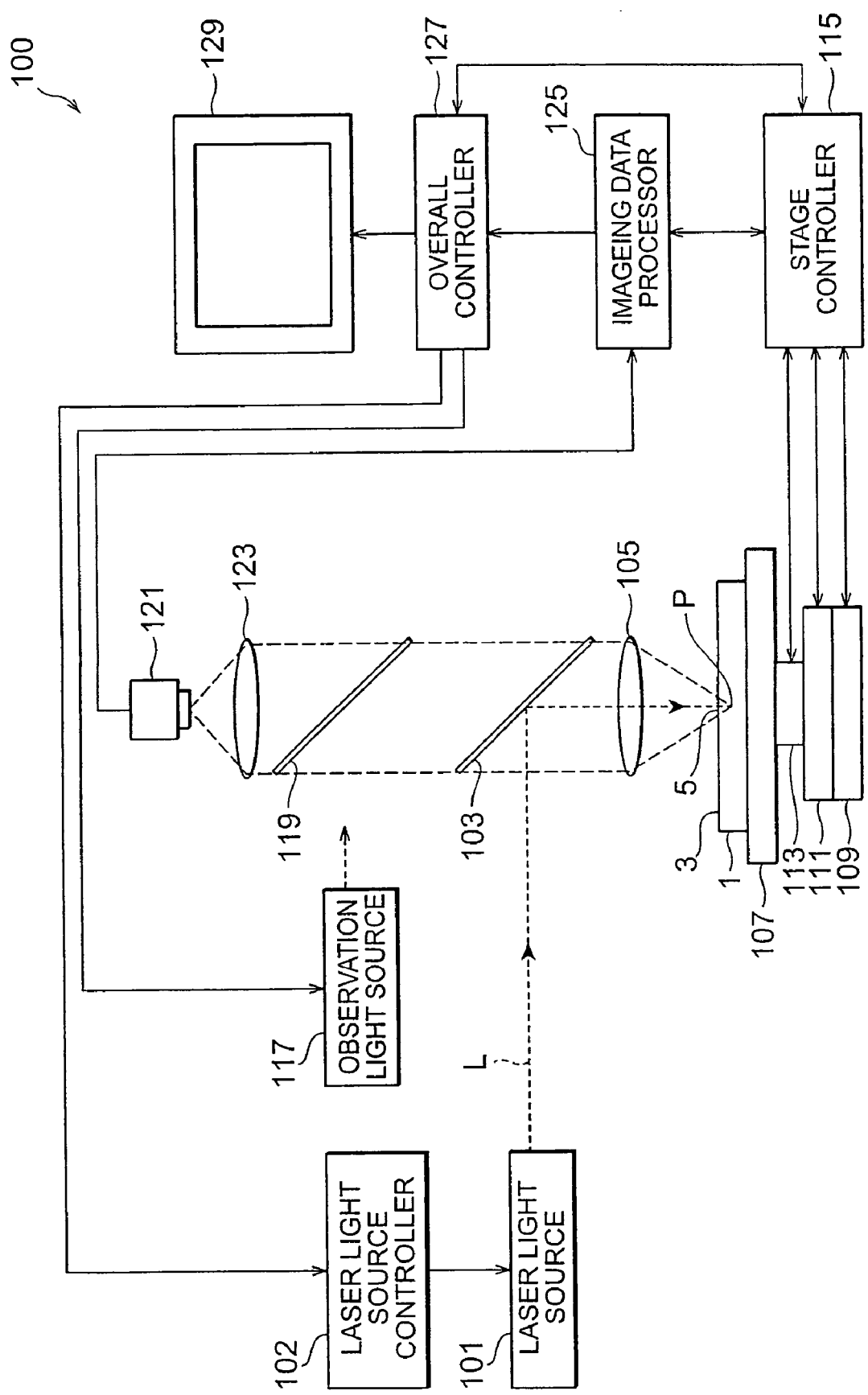
FIG. 14 is a schematic diagram showing the laser processing apparatus in accordance with Example 1.

The laser processing apparatus in accordance with Example 1 will now be explained. FIG. 14 is a schematic diagram of a laser processing apparatus 100 used in the modified region forming step. As depicted, the laser processing apparatus 100 comprises a laser light source 101 for generating laser light L; a laser light source controller 102 for controlling the laser light source 101 in order to regulate the output, pulse width, and the like of the laser light L; a dichroic mirror 103 arranged so as to change the orientation of the optical axis of the laser light L by 90° while functioning to reflect the laser light L; a condenser lens 105 for converging the laser light L reflected by the dichroic mirror 103; a mount table 107 for mounting an object to be processed 1 to be irradiated with the laser light L converged by the condenser lens 105; an X-axis stage 109 for moving the mount table 107 along an X axis; a Y-axis stage 111 for moving the mount table 107 along a Y axis which is orthogonal to the X axis; a Z-axis stage 113 for moving the mount table 107 along a Z-axis which is orthogonal to X and Y axes; and a stage controller 115 for controlling the movement of the three stages 109, 111, 113. In Example 1, the object 1 is a Pyrex (registered trademark) glass wafer.

The Z axis is orthogonal to the front face 3 of the object 1, and thus is the direction of focal depth of the laser light incident on the object 1. Therefore, the light-converging point P of the laser light L can be positioned within the object 1 by moving the Z-axis stage 113 along the Z axis. The movement of the light-converging point P along the X (Y) axis is performed by moving the object 1 along the X (Y) axis by the X (Y)-axis stage 109 (111).

The laser light source 101 is Nd:YAG laser generating pulsed laser light. Other examples of the laser employable in the laser light source 101 include Nd:YVO$_4$ laser and Nd:YLF laser. The above-mentioned laser light sources are preferably used for forming a crack region or a molten processed region, whereas a titanium sapphire laser is preferably used for forming a refractive index change region. Though Example 1 uses pulsed laser light for processing the object 1, continuous wave laser light may also be used if it can cause multiphoton absorption.

The laser processing apparatus 100 further comprises an observation light source 117 for generating visible rays for illuminating the object 1 mounted on the mount table 107, and a visible ray beam splitter 119 disposed on the same optical axis as with the dichroic mirror 103 and condenser lens 105. The dichroic mirror 103 is disposed between the beam splitter 119 and condenser lens 105. The beam splitter 119 functions to reflect about a half of the visible rays and transmit the remaining half therethrough, and is disposed so as to change the orientation of the optical axis of visible rays by 90°. About a half of the visible rays generated from the observation light source 117 are reflected by the beam splitter 119. Thus reflected visible rays pass through the dichroic mirror 103 and condenser lens 105, thereby illuminating the front face 3 of the object 1 including the line 5 along which the object is intended to be cut and the like.

The laser processing apparatus 100 further comprises an image pickup device 121 and an imaging lens 123 which are disposed on the same optical axis as with the beam splitter 119, dichroic mirror 103, and condenser lens 105. An example of the image pickup device 121 is a CCD (charge-coupled device) camera. The reflected light of visible rays having illuminated the front face 3 including the line 5 along which the object is intended to be cut and the like passes through the condenser lens 105, dichroic mirror 103, and beam splitter 119, so as to be focused by the imaging lens 123 and captured by the image pickup device 121, thus yielding imaging data.

The laser processing apparatus 100 further comprises an imaging data processor 125 for inputting the imaging data outputted from the image pickup device 121, an overall controller 127 for controlling the laser processing apparatus 100 as a whole, and a monitor 129. Based on the imaging data, the imaging data processor 125 calculates focal data for positioning the focal point of visible rays generated by the observation light source 117 onto the front face 3. According to the focal data, the stage controller 115 regulates the movement of the Z-axis stage 113, so as to position the focal point of visible rays at the front face 3. Thus, the imaging data processor 125 functions as an autofocus unit. The focal point of visible light coincides with the light-converging point of laser light L. On the basis of imaging data, the imaging data processor 125 calculates image data such as enlarged images of the front face 3. The image data are sent to the overall controller 127, so as to be subjected to various processing operations, and thus processed data are transmitted to the monitor 129. As a consequence, enlarged images and the like are displayed on the monitor 129.

The data from the stage controller 115, the image data from the imaging data processor 125, etc. are fed into the overall controller 127, whereas the laser light source controller 102, observation light source 117, and stage controller 115 are regulated according to these data as well, whereby the laser processing apparatus 100 as a whole is controlled. Hence, the overall controller 127 functions as a computer unit.

Figure 15:
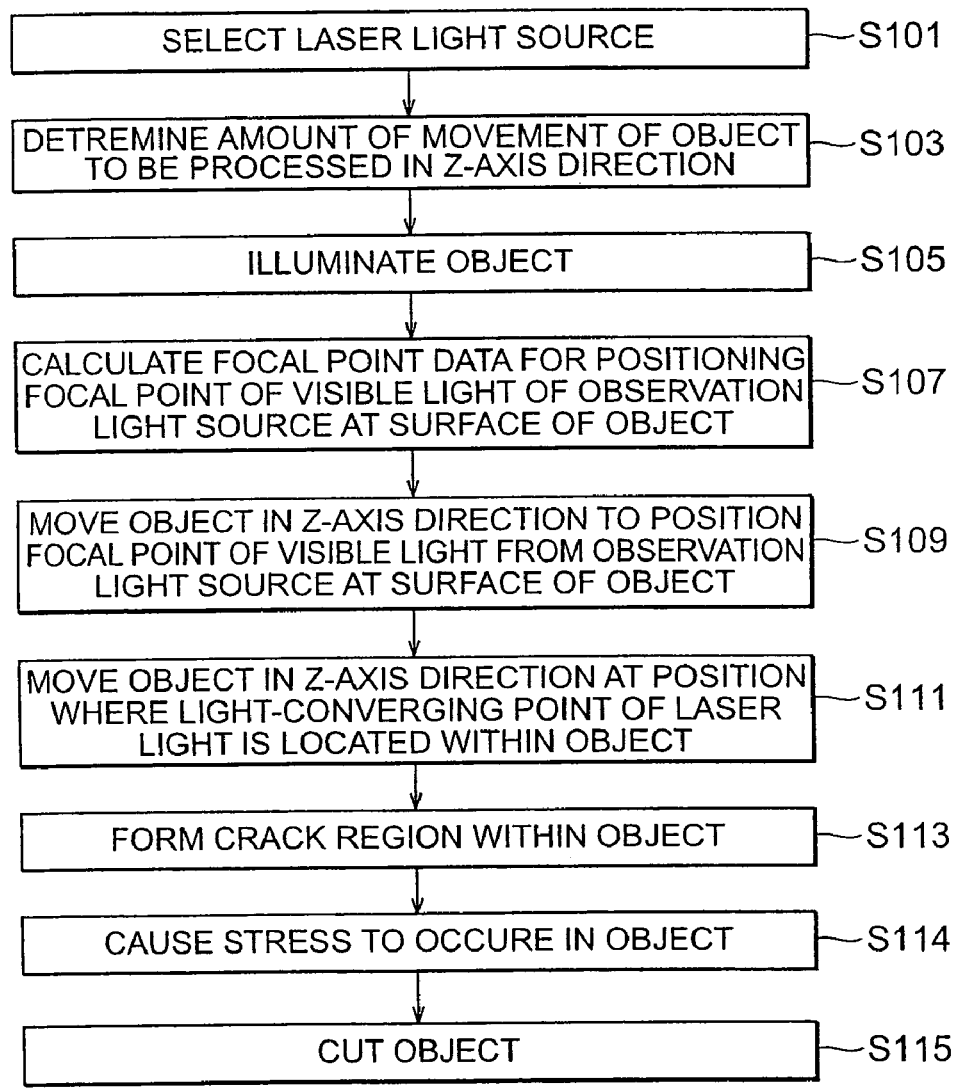
FIG. 15 is a flowchart for explaining the laser processing method in accordance with Example 1.

With reference to FIGS. 14 and 15, the laser processing method in accordance with Example 1 will now be explained. FIG. 15 is a flowchart for explaining the laser processing method.

First, the light absorption characteristic of the object 1 is measured by a spectrophotometer or the like which is not depicted. According to the result of measurement, a laser light source 101 which generates laser light L having a wavelength to which the object 1 is transparent or less absorptive is chosen (S101). Subsequently, the thickness of the object 1 is measured. According to the result of measurement of thickness and the refractive index of the object 1, the amount of movement of the object 1 along the Z axis in the laser processing apparatus 100 is determined (S103). This is an amount of movement of the object 1 along the Z axis with reference to the light-converging point P of laser light L positioned at the front face 3 of the object 1 for locating the light-converging point P of laser light L within the object 1. This amount of movement is fed into the overall controller 127 in the laser processing apparatus 100 used in the modified region forming step.

The object 1 is mounted on the mount table 107 of the laser processing apparatus 100. Then, visible rays are generated from the observation light source 117, so as to illuminate the object 1 (S105). The front face 3 of the object 1 including the illuminated line 5 along which the object is intended to be cut is captured by the image pickup device 121. The imaging data captured by the image pickup device 121 is sent to the imaging data processor 125. According to the imaging data, the imaging data processor 125 calculates such focal data as to position the focal point of visible rays from the observation light source 117 onto the front face 3 (S107).

The focal data is sent to the stage controller 115. According to the focal data, the stage controller 115 moves the Z-axis stage 113 along the Z axis (S109). As a consequence, the focal point of the visible rays from the observation light source 117 is positioned at the front face 3. According to the imaging data, the imaging data processor 125 calculates enlarged image data of the front face 3 of the object 1 including the line 5 along which the object is intended to be cut. The enlarged image data is sent to the monitor 129 by way of the total controller 127, whereby an enlarged image of the line 5 along which the object is intended to be cut and its vicinity is displayed on the monitor 129.

The movement amount data determined by step S103 has been fed into the total controller 127 beforehand, and is sent to the stage controller 115. According to the movement amount data, the stage controller 115 causes the Z-axis stage 113 to move the object 1 along the Z axis to such a position that the light-converging point P of laser light L is located within the object 1 (S111).

Figure 16:
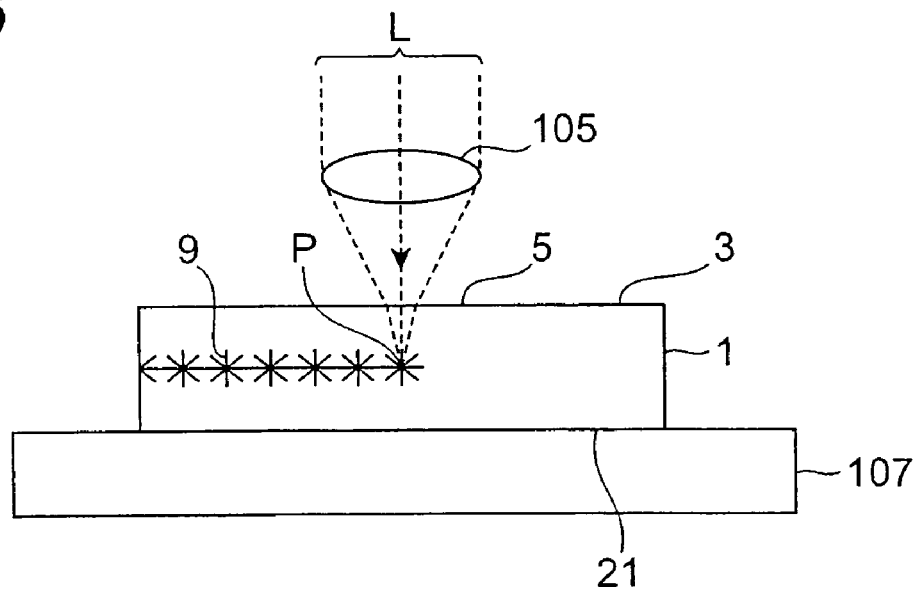
FIG. 16 is a sectional view of the object including a crack region during processing in a modified region forming step in accordance with Example 1.

Subsequently, laser light L is generated from the laser light source 101, so as to illuminate the line 5 along which the object is intended to be cut in the front face 3 of the object 1. FIG. 16 is a sectional view of the object 1 including a crack region 9 during the laser processing in the modified region forming step. Since the light-converging point P of laser light L is located within the object 1 as depicted, the crack region 9 is formed only within the object 1. Then, the X-axis stage 109 and Y-axis stage 111 are moved along the line 5 along which the object is intended to be cut, so as to form the crack region 9 within the object 1 along the line 5 along which the object is intended to be cut (S113).

Figure 17:
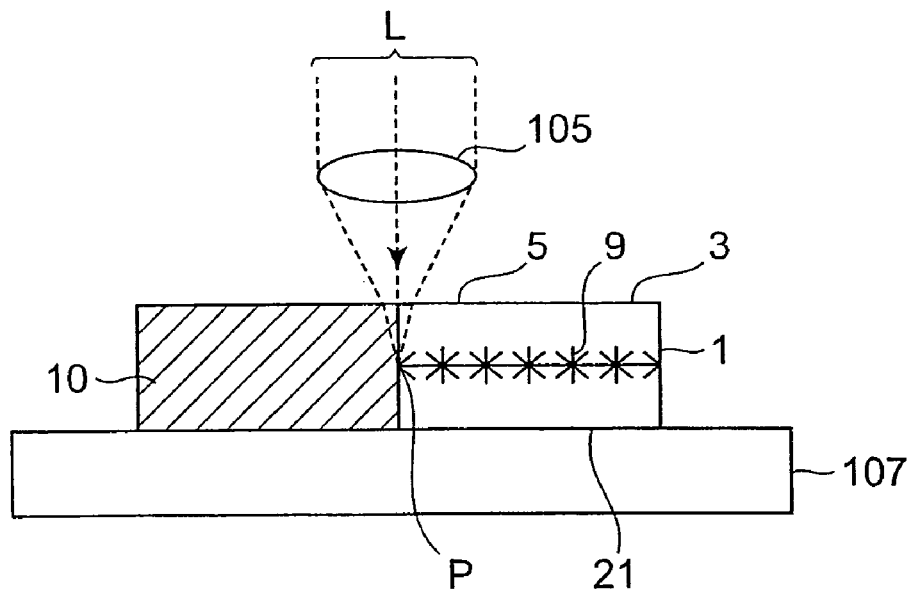
FIG. 17 is a sectional view of the object including the crack region during laser processing in a stress step in accordance with Example 1.

After the modified region is formed, the crack region 9 is irradiated with the laser light L along the line 5 along which the object is intended to be cut in the front face 3 of the object 1 again under the same condition (i.e., while the light-converging point P is located at the crack region 9 that is a modified region). As a consequence, the absorption of laser light L due to scattering and the like by the crack region 9 or the occurrence of multiphoton absorption in the crack region heats the object 1 along the crack region 9, thereby causing a stress such as thermal stress due to a temperature difference (S114). FIG. 17 is a sectional view of the object 1 including the crack region 9 during the laser processing in the stress step. As depicted, cracks further grow and reach the front face 3 and rear face 21 of the object 1 from the crack region 9 acting as a start point, so as to form a cut section 10 in the object 1, thereby cutting the object 1 (S115). This divides the object 1 into silicon chips.

Though the stress step performs the same laser light irradiation as with the modified region in Example 1, it will be sufficient if laser light transmittable through the unmodified region that is the region not formed with the crack region in the object and more absorbable by the crack region than by the unmodified region is emitted. This is because the laser light is hardly absorbed at the front face of the object in this case as well, so that the object is heated along the crack region, whereby a stress such as thermal stress due to a temperature difference occurs.

Though Example 1 relates to a case where a crack region is formed as a modified region, the same holds in cases where the above-mentioned molten processed region and refractive index change region are formed. That is, irradiation with absorbable laser light can cause a stress, so as to generate and grow cracks from the molten processed region or refractive index change region acting as a start point, thereby cutting the object to be processed.

Even when cracks grown from the modified region acting as a start point by the stress step fail to reach the front and rear faces of the object in the case where the object has a large thickness, etc., the object can be fractured and cut by applying an artificial force such as bending stress or shear stress thereto. This artificial force can be kept smaller, whereby unnecessary fractures deviating from the line to cut can be prevented from occurring in the front face of the object.

Effects of Example 1 will now be explained. In this case, the line 5 along which the object is intended to be cut is irradiated with pulsed laser light L while locating a light-converging point P within the object 1 under a condition generating multiphoton absorption in the modified region forming step. Then, the X-axis stage 109 and Y-axis stage 111 are moved, so as to shift the light-converging point P along the line 5 along which the object is intended to be cut. This forms a modified region (e.g., crack region, molten processed region, or refractive index change region) within the object 1 along the line 5 along which the object is intended to be cut. When a start point exists in a portion to cut the object, the object can be fractured and cut with a relatively small force. In Example 1, the stress step performs the same laser irradiation as with the modified region forming step, thereby causing a stress such as thermal stress due to a temperature difference. As a consequence, a relatively small force typified by a stress such as thermal stress due to a temperature difference can cut the object 1. This can cut the object 1 without generating unnecessary fractures deviating from the line 5 along which the object is intended to be cut in the front face 3 of the object 1.

In the modified region forming step in Example 1, since the object 1 is irradiated with pulsed laser light L while locating the light-converging point P within the object 1 under a condition generating multiphoton absorption in the object 1, the pulsed laser light L is transmitted through the object 1, whereby the pulsed laser light is hardly absorbed by the front face 3 of the object 1. The stress step performs the same laser light irradiation as with the modified region forming step. Therefore, the front face 3 does not incur damages such as melting because of irradiation with laser light.

As explained in the foregoing, Example 1 can cut the object 1 without generating unnecessary fractures deviating from the line 5 along which the object is intended to be cut in the front face 3 of the object 1 or melting the same. Therefore, when the object 1 is a semiconductor wafer, for example, semiconductor chips can be cut out from the semiconductor wafer without generating unnecessary fractures deviating from a line to cut in the semiconductor chips or melting the same. The same holds in objects to be processed having a front face formed with electronic devices such as objects to be processed having a front face formed with electrode patterns, piezoelectric device wafers, and glass substrates formed with display devices such as liquid crystals. Hence, Example 1 can improve the yield of products (e.g., semiconductor chips, piezoelectric device chips, and display devices such as liquid crystals) made by cutting objects to be processed.

In Example 1, since the line 5 along which the object is intended to be cut in the front face 3 of the object 1 does not melt, the width of the line 5 along which the object is intended to be cut (which is the gap between respective regions to become semiconductor chips in the case of a semiconductor wafer, for example) can be made smaller. This increases the number of products formed from a single sheet of object to be processed 1, and can improve the productivity of products.

Figure 18:
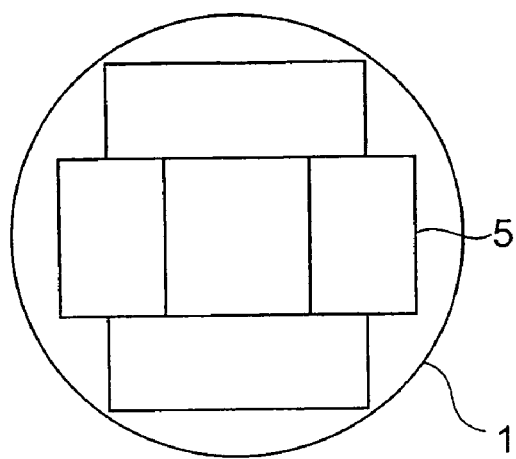
FIG. 18 is a plan view of the object for explaining a pattern which can be cut by the laser processing method in accordance with Example 1.

Example 1 uses laser light for cutting and processing the object 1, and thus enables processing more complicated than that in dicing with diamond cutters. For example, cutting and processing is possible even when lines 5 along which the object is intended to be cut have complicated forms as shown in FIG. 18.

Example 2

Example 2 of the present invention will now be explained. FIGS. 20 to 23 are partial sectional views of the object 1 taken along the line XX-XX of FIG. 19.

Figure 19:
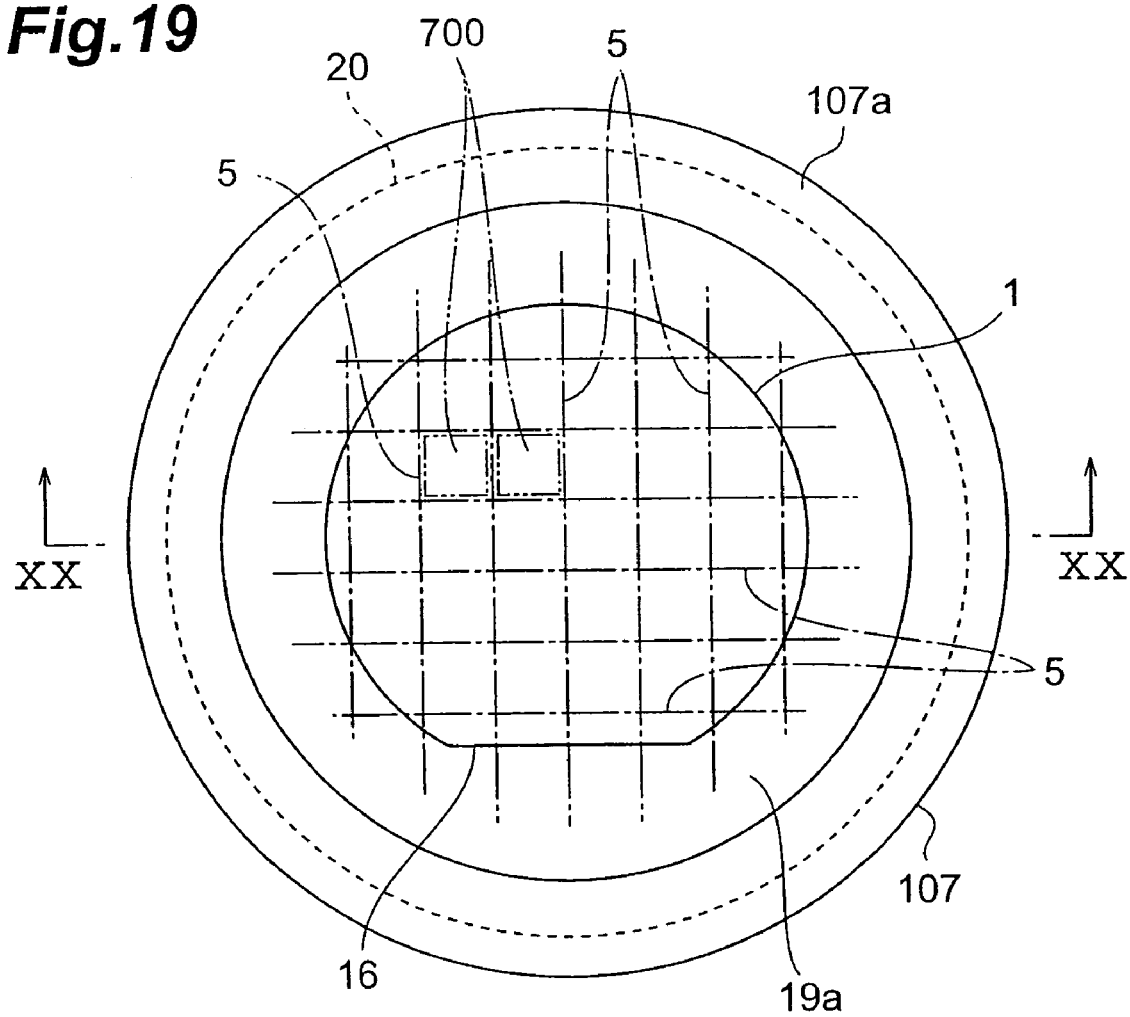
FIG. 19 is a plan view of the object in accordance with Example 2.
Figure 20:
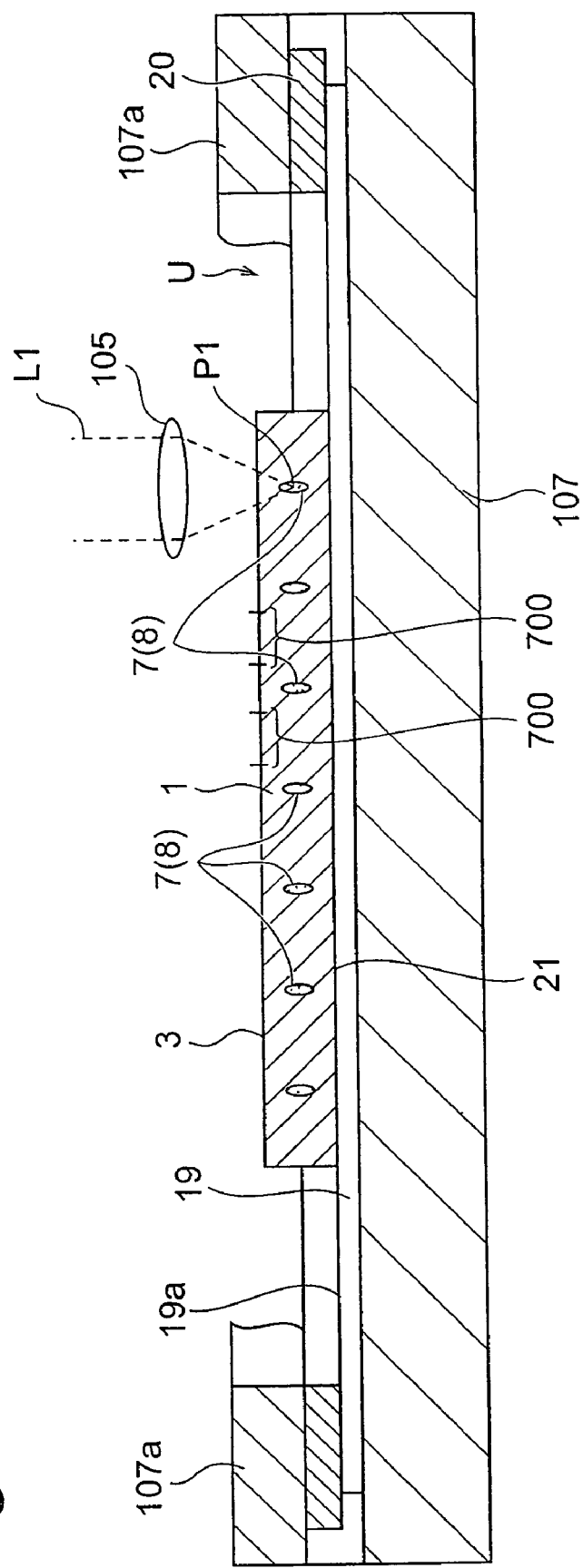
FIG. 20 is a sectional view showing a state where a cutting start region is formed in the object in accordance with Example 2.

As shown in FIGS. 19 and 20, an expandable film (holding member) 19 is attached to the rear face 21 of the object 1, whereas the object 1 is secured onto the front face 19a of the expandable film 19. The expandable film 19 has an outer peripheral part attached to a ring-shaped film securing frame 20, so as to be secured thereto. The object 1 is a silicon wafer having a thickness of 100 μm.

A unit U thus constructed by the object 1, expandable film 19, and film securing frame 20 is mounted on the mount table 107 of the above-mentioned laser processing apparatus 100, for example, such that the front face 3 of the object 1 opposes the condenser lens 105. Then, a holder 107a secures the film securing frame 20 onto the mount table 107, while the expandable film 19 is attracted to the mount table 107 in a vacuum.

Subsequently, as shown in FIG. 19, lines 5 along which the object is intended to be cut extending in directions parallel and perpendicular to an orientation flat 16 of the object 1 are set like a grid. The lines along which the object is intended to be cut are set between device forming surfaces 700 each made of a functional device such as circuit device or light-receiving surface formed on the wafer. For simplicity, the device forming surfaces 700 are illustrated only partly in the drawing.

Then, as shown in FIG. 20, the object 1 is irradiated with laser light L1 while locating a light-converging point P1 within the object 1, and the light-converging point P1 is moved along the lines 5 along which the object is intended to be cut, so as to form a modified region 7 within the object 1. This modified region 7 forms a cutting start region 8 inside of the front face (laser light entrance surface) 3 of the object 1 by a predetermined distance along the lines 5 along which the object is intended to be cut. Since the object 1 is a silicon wafer, a molten processed region is formed as the modified region 7.

Figure 21:
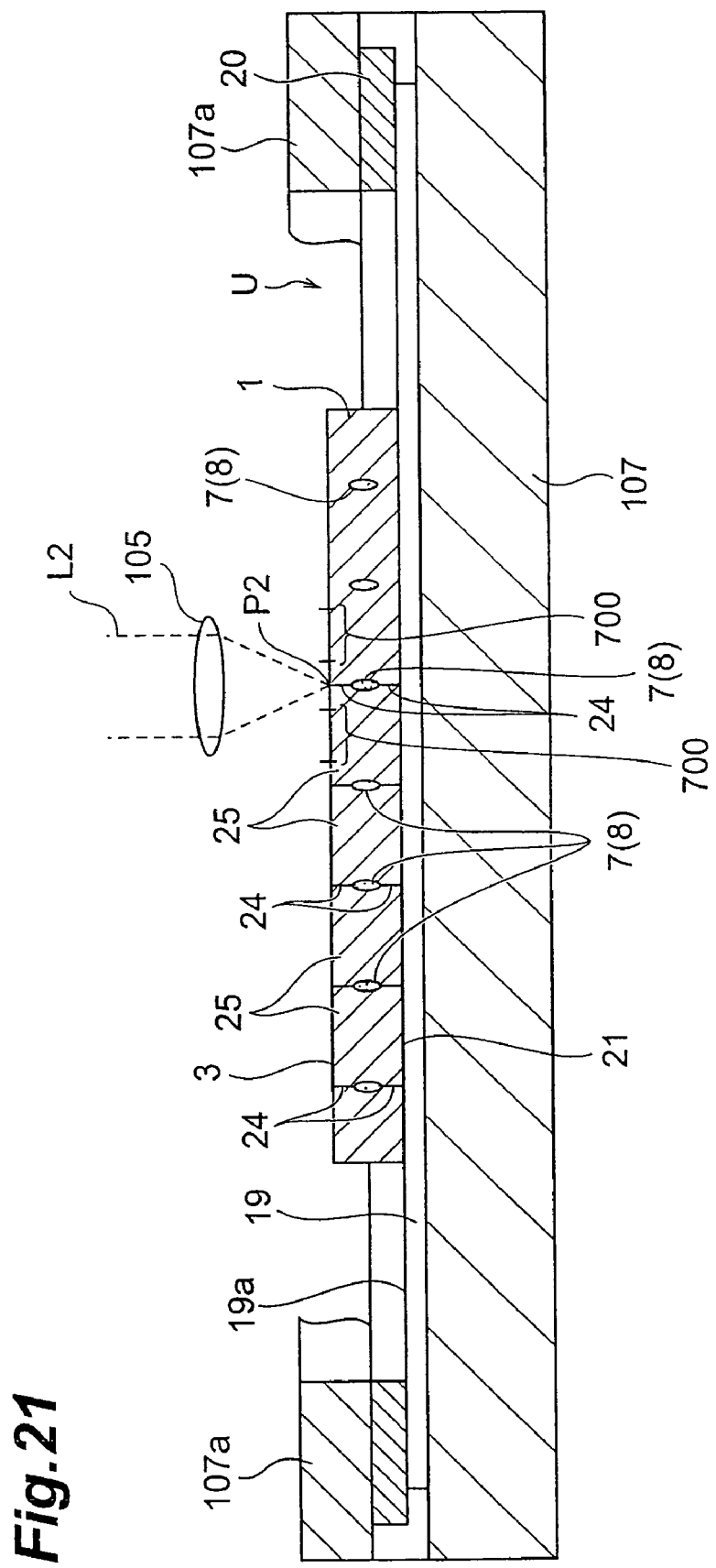
FIG. 21 is a sectional view showing a state where the object in accordance with Example 2 is irradiated with laser light transmittable through an unmodified region of the object and more absorbable by the modified region than by the unmodified region.

Subsequently, as shown in FIG. 21, the object 1 is irradiated with laser light L2 transmittable through the unmodified region of the object 1 (the part other than the modified region 7 in the object 1) and preferably more absorbable by the modified region 7 than by the unmodified region while locating a light-converging point P2 within the modified region 7 of the object 1, and the light-converging point P2 is moved along the lines 5 along which the object is intended to be cut. The irradiation with the laser light L2 generates fractures 24 from the cutting start region 8 acting as a start point, whereby the fractures 24 reach the front face 3 and rear face 21 of the object 1. As a consequence, the object 1 is divided into a plurality of chips 25 along the lines 5 along which the object is intended to be cut. In Example 2, YAG laser having a wavelength of 1064 nm is used as the laser light L2.

A main cause of such fractures 24 is that the object 1 is heated along the lines 5 along which the object is intended to be cut upon irradiation with the laser light L2, whereby a thermal stress occurs in the object 1. For example, upon irradiation with the laser light L2, a boundary between modified and unmodified regions yields continuous irregularities as shown in FIG. 12 instead of a smooth surface, so that the laser light L2 is scattered by the boundary between the modified region 7 and the unmodified region, whereby the part surrounding the modified region 7 is heated. This heat generates fine cracks and distortions in the boundary between the modified region 7 and the unmodified region, so as to cause a tensile stress starting from these cracks and distortions, whereby fractures 24 occur from the modified region 7 to the front face 3 or rear face 21.

Figure 22:
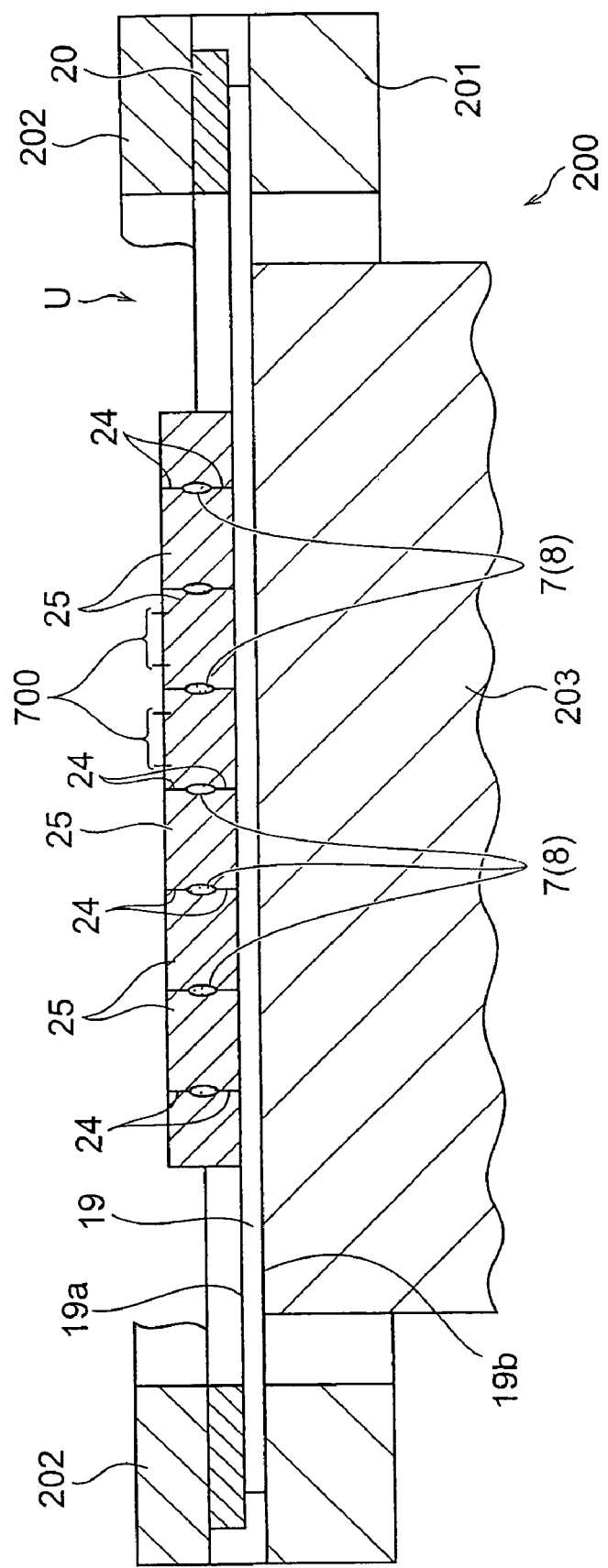
FIG. 22 is a sectional view showing a state where the object in accordance with Example 2 is set to a film expanding apparatus.
Figure 23:
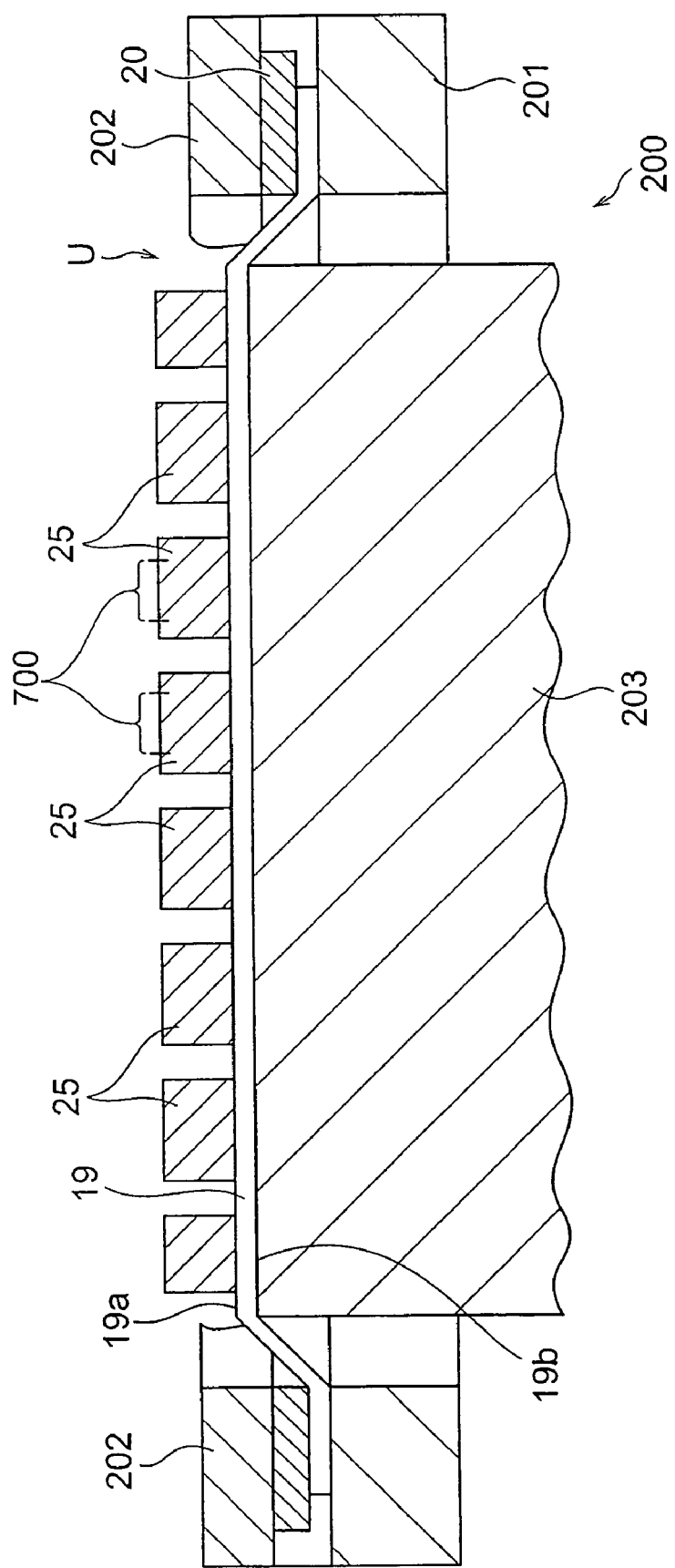
FIG. 23 is a sectional view showing a state where an expandable film having the object in accordance with Example 2 secured thereto is expanded.

After the object 1 is cut into a plurality of chips 25, the unit U is transferred to a film expander 200. As shown in FIG. 22, the unit U has its film securing frame 20 held between a ring-shaped receptacle 201 and a ring-shaped holder 202, so as to be secured to the film expander 200. Then, a cylindrical pressing member 203 disposed on the inside of the receptacle 201 is pressed against the rear face 19b of the expandable film 19 from the lower side of the unit U, and is raised as shown in FIG. 23. This expands contact portions of the individual chips 25 in the expandable film 19 outward, so as to separate the chips 25 from each other, whereby the chips 25 can be picked up easily and reliably.

In the foregoing laser processing method in accordance with Example 2, the modified region 7 formed by multiphoton absorption can form the cutting start region 8 within the object 1 along the lines 5 along which the object is intended to be cut. Irradiating the object 1 with laser light L2 transmittable through the unmodified region of the object 1 (preferably more absorbable by the modified region 7 than by the unmodified region) along the lines 5 along which the object is intended to be cut can generate fractures 24 in the object 1 from the cutting start region 8 acting as a start point, whereby the object 1 can be cut accurately along the lines 5 along which the object is intended to be cut. Expanding the expandable film 19 having the object 1 secured thereto separates the chips 25 from each other, which can further improve the reliability in cutting the object 1 along the line 5 along which the object is intended to be cut.

Example 3

Figure 24:
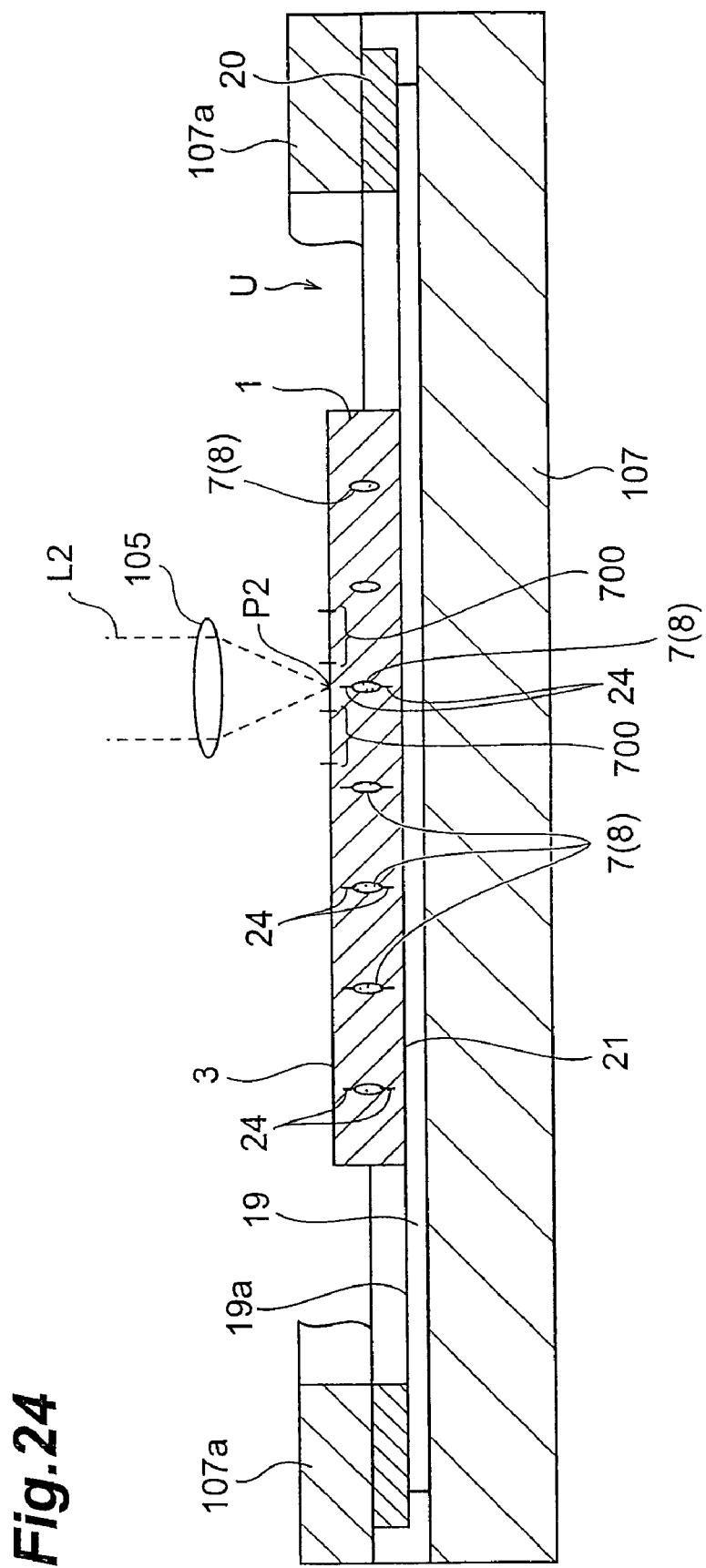
FIG. 24 is a sectional view showing a state where the object in accordance with Example 3 is irradiated with laser light transmittable through the unmodified region of the object and more absorbable by the modified region than by the unmodified region.

Example 3 of the present invention will now be explained. Example 3 differs from Example 2 in that fractures 24 do not reach the front face 3 and rear face 21 of the object 1. In the following, the differences from Example 2 will mainly be explained. FIG. 24 is a partial sectional view of the object 1 taken along the line XX-XX of FIG. 19.

As in Example 2, a unit U constituted by the object 1, an expandable film 19, and a film securing frame 20 is prepared, a modified region 7 is formed within the object 1 by using the above-mentioned laser processing apparatus 100, and a cutting start region 8 is formed by the modified region 7 inside of the front face 3 of the object 1 by a predetermined distance along lines 5 along which the object is intended to be cut. The object 1 is a silicon wafer having a thickness of 300 μm.

Subsequently, as shown in FIG. 24, the object 1 is irradiated with laser light L2 transmittable through the unmodified region of the object 1 and preferably more absorbable by the modified region 7 than by the unmodified region while locating a light-converging point P2 within the modified region 7 of the object 1, and the light-converging point P2 is moved along the lines 5 along which the object is intended to be cut. The irradiation with the laser light L2 generates fractures 24 from the cutting start region 8 acting as a start point. Since the thickness (300 μm) of the object 1 in Example 3 is greater than the thickness (100 μm) of the object 1 in Example 2, the fractures 24 stay therewithin without reaching the front face 3 and rear face 21 of the object 1. The irradiation condition of laser light L2 is the same as that in Example 2.

Next, as in Example 2, the unit U is transferred to the film expander 200. In the film expander 200, the pressing member 203 is pressed against the rear face 19b of the expandable film 19, and is raised. This expands contact portions of the individual chips 25 in the expandable film 19 outward. As the expandable film 19 expands, leading ends of the fractures 24 within the object 1 reach the front face 3 and rear face 21 of the object 1, so that the object 1 is divided into a plurality of chips 25, whereby the chips 25 are separated from each other.

Depending on the irradiation condition of laser light L2, the fractures 24 may not occur upon irradiation with the laser light L2. Even in such a case, expanding the expandable film 19 can cut the object 1 along the lines 5 along which the object is intended to be cut more easily with a higher accuracy than in the case without irradiation with laser light L2.

The foregoing laser processing method in accordance with Example 3 can form the cutting start region 8 within the object 1 along the lines 5 along which the object is intended to be cut as with the above-mentioned laser processing method in accordance with Example 2. Then, irradiating the object 1 with laser light L2 transmittable through the unmodified region of the object 1 (preferably more absorbable by the modified region 7 than by the unmodified region) along the lines 5 along which the object is intended to be cut can cause the fractures 24 started from the cutting start region 8 to reach the front face 3 and rear face 21 of the object 1 with a force smaller than that in the case without such irradiation. Therefore, the expandable film 19 having the object 1 secured thereto can be expanded with a smaller force, and the object 1 can be cut accurately along the lines 5 along which the object is intended to be cut. Expanding the expandable film 19 separates the chips 25 from each other, whereby the reliability in cutting the object 1 along the lines 5 along which the object is intended to be cut can further be improved.

The present invention is not restricted to Examples 1 to 3 mentioned above.

The following are preferred examples of the material of the object 1 and species of laser light L2 transmittable through the unmodified region of the object 1 and more absorbable by the modified region 7 than by the unmodified region. Namely, when the object 1 is a silicon wafer or GaAs-based wafer, laser light having a wavelength of 900 nm to 1100 nm is preferably used as the laser light L2. A specific example is YAG laser (with a wavelength of 1064 nm).

The fractures 24 generated upon irradiation with the laser light L2 may reach one of the front face 3 and rear face 21 of the object 1. Such control is possible when the modified region 7 is formed at a position shifted from the center position in the thickness direction of the object 1 toward the front face 3 or rear face 21. In particular, when the fractures 24 are caused to reach the surface of the object 1 on the expandable film 19 side upon irradiation with the laser light L2, the accuracy in cleaving the object 1 by expanding the expandable film 19 can further be improved.

Here, "the modified region 7 is formed at a position shifted from the center position in the thickness direction of the object 1 toward the front face 3" means that the modified region 7 constituting the cutting start region 8 is formed so as to shift from the half thickness position of the object 1 in the thickness direction toward the front face 3. Namely, it refers to a case where the center position of the width of the modified region in the thickness direction of the object 1 is shifted from the center position of the object 1 in the thickness direction toward the front face 3, without being restricted to the case where the whole modified region 7 is shifted from the center position of the object 1 in the thickness direction toward the front face 3. The same holds in the case where the modified region 7 is formed so as to shift toward the rear face 21 of the object 1.

Though the above-mentioned light-converging point P2 of the laser light L2 is positioned within the modified region 7 of the object 1, it may be positioned in the vicinity of the modified region 7 as long as the modified region 7 is irradiated with the laser light L2.

INDUSTRIAL APPLICABILITY

As explained in the foregoing, the laser processing method in accordance with the present invention can cut the object to be processed accurately along lines along which the object is intended to be cut.

The invention claimed is:

1. A laser processing method comprising the steps of:
   irradiating a wafer-like object to be processed which has a front surface and a rear surface and which is secured to a surface of an expandable holding member with pulsed laser light from a laser light source while focusing a light-converging point within the object, so as to form a modified region only within the object, wherein the modified region forms a cutting start region inside of a laser light entrance surface of the object by a predetermined distance along a line along which the object is to be cut, and wherein any fractures generated from the modified region formed in the step of irradiating the wafer-like object with pulsed laser light do not reach either the front surface or the rear surface of the wafer-like object;
   irradiating the modified region with pulsed laser light from the laser light source transmittable through an unmodified region of the object and more absorbable by the modified region than by the unmodified region after the step of forming the cutting start region, so as to change the cutting start region into one from which it is easier to generate a fracture compared to the cutting start region as configured prior to the step of irradiating the modified region, and cutting the object along the line along which the object is to be cut by causing fractures generated from the modified region to extend from the modified region to the front surface and the rear surface of the wafer-like object; and
   expanding the holding member after the step of cutting the object, so as to separate cut portions of the object from each other.

2. A laser processing method according to claim 1, wherein the step of cutting the object performs the same laser light irradiation as with the step of forming the cutting start region while focusing a light-converging point at the modified region.

3. A laser processing method according to claim 1, wherein the object is formed from a semiconductor material, and wherein the modified region is a molten processed region.

4. A laser processing method comprising the steps of:
   irradiating a wafer-like object to be processed which has a front surface and a rear surface and which is secured to a surface of an expandable holding member with pulsed laser light from a laser light source while focusing a light-converging point within the object, so as to form a modified region only within the object, wherein the modified region forms a cutting start region inside of a laser light entrance surface of the object by a predetermined distance along a line along which the object is to be cut, and wherein any fractures generated from the modified region formed in the step of irradiating the wafer-like object with pulsed laser light do not reach either the front surface or the rear surface of the wafer-like object;

irradiating the modified region with pulsed laser light from the laser light source transmittable through an unmodified region of the object and more absorbable by the modified region than by the unmodified region after the step of forming and cutting start region, so as to change the cutting start region into one from which it is easier to generate a fracture compared to the cutting start region as configured prior to the step of irradiating the modified region; and expanding the holding member after the step of changing the cutting start region, so as to cut the object by causing fractures generated from the modified region to extend from the modified region to the front surface and the rear surface of the wafer-like object and so as to separate cut portions of the object from each other.

5. A laser processing method according to claim 4, wherein the step of changing the cutting start region performs the same laser light irradiation as with the step of forming the cutting start region while focusing a light-converging point at the modified region.

6. A laser processing method according to claim 4, wherein the object is formed from a semiconductor material, and wherein the modified region is a molten processed region.

7. A laser processing method comprising the steps of:

irradiating a wafer-like object to be processed which has a front surface and a rear surface and which is secured to a surface of an expandable holding member with pulsed laser light from a laser light source while focusing a light-converging point within the object, so as to form a modified region only within the object, wherein the modified region forms a cutting start region inside of a laser light entrance surface of the object by a predetermined distance along a line along which the object is to be cut, and wherein any fractures generated from the modified region formed in the step of irradiating the wafer-like object with pulsed laser light do not reach either the front surface or the rear surface of the wafer-like object;

irradiating the modified region with pulsed laser light from the laser light source transmittable through an unmodified region of the object and more absorbable by the modified region than by the unmodified region after the step of forming the cutting start region, so as to change the cutting start region into one from which it is easier to generate a fracture compared to the cutting start region as configured prior to the step of irradiating the modified region, and cutting the wafer-like object by causing fractures generated from the modified region to extend from the modified region to the front surface and the rear surface of the wafer-like object; and expanding the holding member so as to separate cut portions of the object from each other.

8. A laser processing method according to claim 7, wherein both irradiating steps comprise performance of laser irradiation including focusing of a light-converging point at the modified region.

9. A laser processing method according to claim 7, wherein the object is formed from a semiconductor material, and wherein the modified region is a molten processed region.

* * * * *